United States Patent
Xia et al.

(10) Patent No.: US 10,982,209 B2
(45) Date of Patent: Apr. 20, 2021

(54) READ THROUGH OF TRUNCATED PROTEINS IN PREMATURE TERMINATION CODON DISEASES BY SUPPRESSOR TRNAS

(71) Applicant: PEKING UNIVERSITY, Beijing (CN)

(72) Inventors: Qing Xia, Beijing (CN); Tianchang Wang, Beijing (CN); Qi Yang, Beijing (CN)

(73) Assignee: PEKING UNIVERSITY, Beijing (CN)

(*) Notice: Subject to any disclaimer, the term of this patent is extended or adjusted under 35 U.S.C. 154(b) by 219 days.

(21) Appl. No.: 16/083,772

(22) PCT Filed: Mar. 3, 2017

(86) PCT No.: PCT/CN2017/075581
§ 371 (c)(1),
(2) Date: Sep. 10, 2018

(87) PCT Pub. No.: WO2017/152809
PCT Pub. Date: Sep. 14, 2017

(65) Prior Publication Data
US 2019/0119675 A1 Apr. 25, 2019

(30) Foreign Application Priority Data
Mar. 10, 2016 (CN) .......................... 201610134656.1

(51) Int. Cl.
| | |
|---|---|
| *C12N 15/113* | (2010.01) |
| *A61P 21/00* | (2006.01) |
| *A61P 35/00* | (2006.01) |
| *A61K 48/00* | (2006.01) |
| *C12N 15/63* | (2006.01) |
| *C12N 15/11* | (2006.01) |

(52) U.S. Cl.
CPC ............ *C12N 15/113* (2013.01); *A61K 48/00* (2013.01); *A61P 21/00* (2018.01); *A61P 35/00* (2018.01); *C12N 15/11* (2013.01); *C12N 15/63* (2013.01); *C12N 2310/10* (2013.01)

(58) Field of Classification Search
None
See application file for complete search history.

(56) References Cited

U.S. PATENT DOCUMENTS

2002/0156042 A1 10/2002 Panchal et al.

OTHER PUBLICATIONS

Bannister et al., Comparison of chicken 7SK and U6 RNA polymerase III promoters for short hairpin RNA expression, BMC Biotechnol., 7:79 (Nov. 19, 2007).
Dooley et al., Duchenne muscular dystrophy: a 30-year population-based incidence study, Clin. Pediatr. (Phila.), 49(2):177-9 (Feb. 2010).
International Application No. PCT/CN2017/075581, International Search Report, dated Jun. 7, 2017.
Keeling et al., Suppression of premature termination codons as a therapeutic approach, Crit. Rev. Biochem. Mol. Biol., 47(5):444-63 (Sep. 2012).
Kiselev et al., [Suppression of nonsense mutations in the Dystrophin gene by a suppressor tRNA gene], Mol Biol. (Mosk.), 36(1):43-7 (Jan.-Feb. 2002).
Köhrer et al., Complete set of orthogonal 21st aminoacyl-tRNA synthetase-amber, ochre and opal suppressor tRNA pairs: concomitant suppression of three different termination codons in an mRNA in mammalian cells, Nucleic Acids Res., 32(21):6200-11 (2004).
Zhouravleva et al., Termination of translation in eukaryotes is governed by two interacting polypeptide chain release factors, eRF1 and eRF3, EMBO J., 14(16):4065-72 (1995).

*Primary Examiner* — Sean McGarry
(74) *Attorney, Agent, or Firm* — Marshall, Gerstein & Borun LLP

(57) ABSTRACT

Provided are a method for constructing a suppressor tRNA, and 19 suppressor tRNAs corresponding to three termination codons, a plasmid, a vector or a kit comprising the above-mentioned tRNA. Also provided are use of the above-mentioned tRNA, plasmid, vector or kit in the manufacture of a medicament for treating a hereditary disease or a cancer caused by a nonsense mutation of a gene. Also provided are a method for evaluating the efficiency of a suppressor tRNA for reading through a nonsense mutation, and a method for restoring the expression of a truncated protein of a nonsense mutant of a pathogenic gene in a monogenic hereditary disease and a tumor suppressor gene in a tumor cell.

4 Claims, 3 Drawing Sheets

Specification includes a Sequence Listing.

READ THROUGH OF TRUNCATED PROTEINS IN PREMATURE TERMINATION CODON DISEASES BY SUPPRESSOR TRNAS

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "53466_Seqlisting.txt", which was created on Sep. 7, 2018 and is 24,165 bytes in size. The subject matter of the Sequence Listing is incorporated herein in its entirety by reference.

TECHNICAL FIELD

The invention belongs to the field of biopharmaceutics, and particularly relates to extending a truncated protein of a nonsense mutant of a pathogenic gene by constructing a suppressor tRNA, thereby producing a full-length functional protein in a mammalian cell so as to restore the normal structure and function of the mutant. The present invention mainly relates to the construction of suppressor tRNAs corresponding to three stop codons, which read through dystrophin protein in a mammalian cell and read through a nonsense mutant protein in a tumor cell, and the effect is remarkable.

BACKGROUND

Nonsense Mutations and the Diseases Caused by them

There are many types of genetic mutations in the human genome, and nonsense mutations belong to one type of genetic mutations. Genetic mutations are heritable variations occurred in genomic DNA molecules, including frameshift mutations and base substitutions. Frameshift mutations include insertions and deletions of bases, while base substitutions are mainly missense mutations and nonsense mutations. A nonsense mutation refers to the mutation of a certain base of the coding gene, resulting in stop codons UAG, UAA and UGA, and the stop codon does not encode any amino acid. The stop codon cannot be paired with an anticodon of a transfer RNA (tRNA), but can be recognized by a termination factor or a release factor, so as to terminate the synthesis of a peptide bond to terminate protein synthesis, and thus produces an incomplete and non-functional protein. The occurrence of nonsense mutations causes premature termination codons (PTC) in the gene box, which leads to two results of genetic coding, one produces a truncated protein and the other results in the decrease of the stability of the mRNA containing PTC, so as to leads to a corresponding hereditary disease. According to statistics, about 11.2% of monogenic hereditary diseases produce PTC mutations, called premature termination codons diseases (PTC diseases). On the other hand, many cancers also produce PTC mutations (KEELING K. M. et al. Critical reviews in biochemistry and molecular biology, 2012, 47: 444-463.).

Duchenne muscular dystrophy (DMD) is a typical representative of PTC diseases. DMD is a serious muscle atrophy disease and the most common X-linked recessive hereditary disease. It is mainly characterized by progressivity and lethality. Nonsense mutations in the DMD gene are one of the main causes of DMD. Nonsense mutations produce premature termination codons UAG, UAA, UGA, resulting in a truncated polypeptide product that causes the patient to loss or lack functional dystrophin, which leads to muscle atrophy. According to reports, the incidence of Duchenne muscular dystrophy in live born baby boys is 1/6300 to 1/3500 [Dooley J. et al. Clin Pediatr (Phila), 2010, 49:177-179.]. There is no effective method for curing this disease now. The onset of this disease mainly appears in childhood. It leads to loss of walking ability in adolescence, and early death in adulthood. It causes heavy psychological and economic burdens on patients, their families and the society.

Read-Through of Nonsense Mutations by Suppressor tRNAs 61 codons in human genome can be recognized by tRNAs, which encode 20 amino acids. The three stop codons (UAG, UAA, UGA) have no corresponding tRNA recognition, and do not encode amino acids, and thus terminate translation. However, studies have found that there are tRNAs that recognize stop codons, such that the stop codons encode amino acids, and protein translation proceeds normally. Such tRNAs capable of recognizing the stop codons are nonsense mutation-suppressing tRNAs. Suppressor tRNAs are widely available, and are found in both plant and animal cells. However, since the amount of suppressive tRNAs is extremely small in cells, suppressor tRNAs are not easily detected.

The nonsense mutation-suppressing tRNA is produced by a base mutation in the anticodon loop of a tRNA normally encoding an amino acid. The mutated tRNA can recognize a stop codon and is fully complementary to the stop codon. In the meantime, it still carries an amino acid, and is capable of inserting a specific amino acid at a premature termination codon and read through a nonsense mutation. Based on the ability of a suppressor tRNA to read through a nonsense mutation, it has been reported in the literature to use the suppressor tRNA to read through a protein comprising a premature termination codon in a prokaryotic and eukaryotic cell to restore the expression of the protein. Since approximately 30% of human hereditary diseases have PTCs but it is still unclear whether a suppressor tRNA is useful for reading through a human hereditary disease-related protein, it is important to extend a truncated protein of a nonsense mutant of a pathogenic gene by constructing a suppressor tRNA to produce a full-length functional protein in a mammalian cell so as to restore the normal structure and function of the mutant. On the other hand, although a suppressor tRNA can restore the expression of a protein comprising a nonsense mutation, it is still unclear how different are read-through efficiency among different suppressor tRNAs. Therefore, it is important to construct a variety of suppressor tRNAs to compare the difference of the read-through efficiency in mammalian cells, and to find efficient suppressor tRNAs.

SUMMARY OF THE INVENTION

After considering and studying the prior art, the inventors have constructed 19 nonsense mutation-suppressing tRNAs (sequences as shown in SEQ ID NOs: 1-19), which carry corresponding amino acids and are fully complementary to premature termination codons, read through nonsense mutations and restore the expression of pathogenic proteins in PTC diseases, and have made comparison to obtain the suppressor tRNAs having the highest efficiency for reading-through nonsense mutations. The inventors firstly identified 19 amino acid codons with higher frequencies of nonsense mutations in human hereditary diseases, changed the corresponding tRNA anticodon loop bases that recognize these 19 codons, constructed nonsense mutation-suppressing tRNAs by the method of SOE PCR, and ligating a 7sk promoter at the 5' end of the suppressor tRNAs. The suppressor tRNAs and dystrophin protein gene containing premature termination codons were then transfected into 293T cells to restore dystrophin protein expression in mammalian cells. At the same time, a dual luciferase reporter gene and a GFP reporter gene containing a stop codon were used to compare the efficiency of different suppressor tRNAs for facilitating the read-through. The suppressor tRNAs having the highest read-through efficiency obtained by comparison were Amber suppressor tRNA (Gln); Ocher suppressor tRNA (Gln); and Opal suppressor tRNA (Arg).

The advantages of the invention may be embodied in one or more of the following:

1. Rapid construction of any one of the suppressor tRNAs is achieved by the method of SOE PCR.

2. Three suppressor tRNAs capable of efficiently reading through nonsense mutations, Amber suppressor tRNA (Gln); Ocher suppressor tRNA (Gln); Opal suppressor tRNA (Arg), were obtained 3. By using a variety of suppressor tRNAs, read-through of nonsense mutations in monogenic hereditary diseases and tumors is achieved, and the normal structure and function of truncated proteins are restored.

In one aspect, the invention relates to a method for rapidly constructing a suppressor tRNA, wherein the method comprises the following steps:

(1) Designing upstream and downstream primers covering all suppressor tRNAs and partially complementary, and designing 7sk gene PCR primers, wherein the 7sk gene PCR downstream primer is complementary to both 7sk and the suppressor tRNA, (2) synthesizing and amplifying the suppressor tRNA, and amplifying a 7sk promoter sequence using the corresponding primers respectively in the first step of PCR;

(3) ligating the suppressor tRNA with the 7sk promoter, and amplifying the product of the ligation to obtain a suppressor tRNA comprising the 7sk promoter in the second step of PCR;

wherein the suppressor tRNA is obtained by a mutation in the anticodon loop of a tRNA.

According to any aspect of the invention, the 7sk promoter sequence is a sequence shown in Table 1.

According to any aspect of the invention, the primer is selected from the sequences shown in Table 2.

In one aspect, the invention relates to a method for screening a suppressor tRNA, comprising:

(1) determining 19 amino acid codons having higher frequencies of nonsense mutations in human hereditary diseases, and identifying bases of the corresponding tRNA anticodon loops of the 19 codons;

(2) constructing a nonsense mutation-suppressing tRNA and ligating a 7sk promoter at the 5' end of the suppressor tRNA;

(3) transfecting the suppressor tRNA and a gene encoding a mutant protein containing a premature termination codon into a host animal cell to restore normal expression of the mutant protein in the host cell;

(4) comparing the efficiency of different suppressor tRNAs for facilitating the read-through to obtain the suppressor tRNA with high read-through efficiency by comparison.

According to any aspect of the invention, the host cell can be a prokaryotic cell, such as an *E. coli* cell, an insect cell, or a eukaryotic cell, such as a yeast cell, a mammalian cell, a tumor cell.

According to any aspect of the invention, the suppressor tRNA obtained by the method is selected from the group consisting of the suppressor tRNAs set forth in SEQ ID NOs: 1-19.

According to any aspect of the invention, the mutant protein is selected from the group consisting of dual luciferase reporter protein, GFP protein, dystrophin protein, STK11 protein, and EPHB2 protein.

In one aspect, the invention relates to a suppressor tRNA obtained by the method of any aspect of the invention.

A suppressor tRNA of any aspect of the invention, wherein the suppressor tRNA is selected from the group consisting of the suppressor tRNAs set forth in SEQ ID NOs: 1-19.

In one aspect, the invention relates to a plasmid, a vector or a kit comprising the tRNA of any aspect of the invention.

A kit according to any aspect of the invention, which comprises a suppressor tRNA having the sequence set forth in any one of SEQ ID NOs: 1-19.

A kit according to any aspect of the present invention, characterized in that it comprises Amber suppressor tRNA (Gln) corresponding to SEQ ID NO: 1; Ocher suppressor tRNA (Gln) corresponding to SEQ ID NO: 14; Opal suppressor tRNA (Arg) corresponding to SEQ ID NO: 7.

In one aspect, the invention relates to use of the tRNA, plasmid, vector or kit of any aspect of the invention, in the manufacture of a medicament for the treatment of a hereditary disease or cancer, wherein the hereditary disease or cancer is caused by a nonsense mutation in a gene. Preferably, the hereditary disease or cancer is caused by a nonsense mutation occurred in Dystrophin protein, tumor suppressor gene STK11 or EPHB2 protein.

The use of any aspect of the invention, wherein the hereditary disease and cancer are selected from the group consisting of: Duchenne muscular dystrophy, cystic fibrosis, hemophilia A, hemophilia B, lipid storage, ataxia telangiectasia, Hurler's syndrome, amaurotic familial idiocy, stomach cancer, and lung cancer.

In one aspect, the invention relates to a method for assessing the efficiency of a suppressor tRNA for reading through a nonsense mutation, comprising:

(1) point mutating a report gene to obtain a mutant comprising UAG, UAA or UGA premature termination codon, and ligating it to an appropriate vector;

(2) co-transfecting the vector comprising the mutant reporter gene obtained in step (1) and different suppressor tRNAs into a host cell;

(3) detecting the reporter gene, and determining the read-through efficiency of the suppressor tRNA according to the detection result of the reporter gene.

The method of any aspect of the invention, wherein the reporter gene is selected from the group consisting of dual luciferase reporter protein, GFP protein, dystrophin protein, STK11 protein, and EPHB2 protein.

In one aspect, the invention relates to a method for restoring the expression of a truncated protein of a nonsense mutant of a pathogenic gene in a monogenic hereditary disease and a tumor suppressor gene in a tumor cell, comprising introducing the tRNA or the plasmid or the vector of any aspect of the invention into a cell or an organism comprising a nonsense mutant protein, preferably using the kit of any aspect of the invention.

In one aspect, the invention relates to obtaining a full length functional protein by using a suppressor tRNA to read through a nonsense mutation site in a monogenic disease and a tumor cell.

The suppressor tRNA according to any aspect of the present invention, which comprises a suppressor tRNA species corresponding to an amino acid in which a nonsense mutation may occur in a hereditary disease, that is, all suppressor tRNAs corresponding to 20 amino acids, characterized in that the suppressor tRNA is fully complementary to a stop codon and the suppressor tRNA is obtained by a mutation in the anticodon loop of a tRNA.

The suppressor tRNA of any aspect of the invention, characterized in that the 5' end of the suppressor tRNA is ligated to a 7sk promoter.

The suppressor tRNA of any aspect of the invention, which is obtained by the following method of SOE PCR:

(1) designing upstream and downstream primers covering all suppressor tRNAs and partially complementary, and designing 7sk gene PCR primers, wherein the 7sk gene PCR downstream primer is complementary to both 7sk and the suppressor tRNA, (2) synthesizing and amplifying the suppressor tRNA, and amplifying a 7sk promoter sequence using the corresponding primers respectively in the first step of PCR;

(3) ligating the suppressor tRNA with the 7sk promoter, and amplifying the product of the ligation to obtain 19 suppressor tRNAs comprising the 7sk promoter in the second step of PCR.

The suppressor tRNAs obtained by the method of any aspect of the invention, which are respectively stRNAGln-UAG having the sequence corresponding to SEQ ID NO: 1; stRNATyr-UAG having the sequence corresponding to SEQ ID NO: 2; stRNALys-UAG having the sequence SEQ ID NO: 3; stRNALeu-UAG having the sequence corresponding to SEQ ID NO: 4; stRNAGlu-UAG having the sequence corresponding to SEQ ID NO: 5; stRNATrp-UAG having the sequence corresponding to SEQ ID NO: 6; stRNAArg-UGA having the sequence corresponding to SEQ ID NO: 7; stRNAGln-UGA having the sequence corresponding to SEQ ID NO: 8; stRNATrp-UGA having the sequence corresponding to SEQ ID NO: 9; stRNAGly-UGA having the sequence corresponding to SEQ ID NO: 10; stRNACys-UGA having the sequence corresponding to SEQ ID NO: 11; stRNALeu-UGA having the sequence corresponding to SEQ ID NO: 12; stRNASer-UGA having the sequence corresponding to SEQ ID NO: 13; stRNAGln-UAA having the sequence corresponding to SEQ ID NO: 14; stRNATyr-UAA having the sequence corresponding to SEQ ID NO: 15; stRNALys-UAA having the sequence corresponding to SEQ ID NO: 16; stRNAGlu-UAA having the sequence corresponding to SEQ ID NO: 17; stRNALeu-UAA having the sequence corresponding to SEQ ID NO: 18; stRNASer-UAA having the sequence corresponding to SEQ ID NO: 19.

The suppressor tRNA of any aspect of the invention, which is ligated to Bjmu vector as set forth in SEQ ID NO: 20 by enzyme cutting.

The suppressor tRNAs according to any aspect of the invention, which are respectively Bjmu-stRNAGln-UAG; Bjmu-stRNATyr-UAG; Bjmu-stRNALys-UAG; Bjmu-stRNALeu-UAG; Bjmu-stRNAGlu-UAG; Bjmu-stRNATrp-UAG; Bjmu-stRNAArg-UGA; Bjmu-stRNAGln-UGA; Bjmu-stRNATrp-UGA; Bjmu-stRNAGly-UGA; Bjmu-stRNACys-UGA; Bjmu-stRNALeu-UGA; Bjmu-stRNASer-UGA; Bjmu-stRNAGln-UAA; Bjmu-stRNATyr-UAA; Bjmu-stRNALys-UAA; Bjmu-stRNAGlu-UAA; Bjmu-stRNALeu-UAA; Bjmu-stRNASer-UAA.

The suppressor tRNAs of any aspect of the invention, wherein the difference in the efficiency thereof for reading through nonsense mutations is obtained by the following steps:

(1) point mutating the GFP fluorescent gene pcDNA3.1-GFP having the original sequence of SEQ ID NO: 21 to obtain pcDNA3.1-GFP-39TAG; pcDNA3.1-GFP-39TAA; pcDNA3.1-GFP-39TGA vectors respectively comprising three premature termination codons, UAG, UAA and UGA;

(2) co-transfecting the luciferase reporter genes pGL4-2luc-TAG; pGL4-2luc-TAA; pGL4-2luc-TGA having the sequence of SEQ ID NO: 22 and different suppressor tRNAs into 293T cells respectively; on the other hand, also co-transfecting the pcDNA3.1-GFP-39TAG; pcDNA3.1-GFP-39TAA; pcDNA3.1-GFP-39TGA vectors and different suppressor tRNAs into 293T cells respectively;

(3) detecting the fluorescence readings of the luciferase reporter genes Firefly and Renila, and reflecting the difference in read-through efficiency according to the relative fluorescence value of Firefly relative to Renila, and determining the read-through efficiency of the tRNAs according to the luorescence intensity of GFP, and finally determining Amber suppressor tRNA (Gln), Ocher suppressor tRNA (Gln) and Opal suppressor tRNA (Arg) as suppressor tRNAs having the highest efficiency for reading through UAG, UAA and UGA respectively.

The method for restoring the expression of a truncated protein of a nonsense mutant of a pathogenic gene in a monogenic hereditary disease and a tumor suppressor gene in a tumor cell by the tRNA of any aspect of the present invention, comprising the following steps:

(1) corresponding Dp71b gene having the sequence of SEQ ID NO: 23 to a position where a mutation is required according to the position of a nonsense mutation in a human DMD disease to mimic the DMD gene sequence in the human DMD disease;

(2) obtaining Dp71b3115TAG comprising the premature termination codon UAG, Dp71b3216TAA comprising the premature termination codon UAA and Dp71b3112TGA comprising the premature termination codon UGA by point mutation technology;

(3) co-transfecting different suppressor tRNAs and the mutated plasmid Dp71b into 293T, or transfecting the suppressor tRNAs a into tumor cells A549 and DU145, harvesting the cells after appropriate time;

(4) detecting the expression of Dp71b in 293T cells, and the expression of STK11 protein and the full length EPHB2 protein in A549 and DU145. It has been found that the suppressor tRNAs can restore the expression of the truncated protein of the nonsense mutant of the pathogenic gene in the monogenic hereditary disease and the tumor suppressor gene in the tumor cell, and different suppressor tRNAs have different recovery efficiency.

DETAILED DESCRIPTION

Specifically, in one embodiment of the present invention, suppressor tRNAs were constructed and the expression of DMD disease-associated protein, dystrophin protein was restored in 293T cells mainly by the following: (1) Expression vectors comprising 19 suppressor tRNAs with a 7sk promoter were constructed, wherein said 19 suppressor tRNAs were Bjmu-stRNAGln-UAG; Bjmu-stRNALyr-UAG; Bjmu-stRNALeu-UAG; Bjmu-stRNALlu-UAG; Bjmu-stRNATrp-UAG; Bjmu-stRNAArg-UGA; Bjmu-stRNAGln-UGA; Bjmu-stRNATrp-UGA; Bjmu-stRNAGly-UGA; Bjmu-stRNACys-UGA; Bjmu-stRNALeu-UGA; Bjmu-stRNASer-UGA; Bjmu-stRNAGln-UAA; Bjmu-stRNATyr-UAA; Bjmu-stRNALys-UAA; Bjmu-stRNAGlu-UAA; Bjmu-stRNALeu-UAA; Bjmu-stRNASer-UAA. The 19 suppressor tRNAs corresponded to 19 amino acid codons that are more susceptible to nonsense mutations; (2) Dual luciferase reporter systems pGL4-2luc-TAG; pGL4-2luc-TAA; pGL4-2luc-TGA comprising stop codons therein, and GFP reporter genes pcDNA3.1-GFP-39TAG; pcDNA3.1-GFP-39TAA; pcDNA3.1-GFP-39TGA comprising premature termination codons were constructed; (3) According to the sites of nonsense mutations in DMD patients, Dp71b protein plasmids Dp71b3115TAG; Dp71b3216TAA; Dp71b3112TGA comprising the premature termination codons UAG, UAA, UGA respectively were constructed by introducing premature termination codons into the corresponding sites of the isoform protein of dystrophin protein, Dp71b by the point mutation technology; (4) The vectors of step (1) and (2) were co-transfected into 293T cells respectively, and the difference in read-through efficiency of different suppressor tRNAs was compared using the dual luciferase system and the GFP reporter system; (5) The suppressor tRNAs of step (1) and the Dp71b proteins comprising the premature termination codons of step (3) were co-transfected into 293T cells respectively, and the restoration of the expression of Dp71b was detected by western blot method. Finally, it was confirmed that various suppressor tRNAs could restore the expression of the nonsense mutated Dp71b proteins, wherein the suppressor tRNA (Gln) has higher read-through efficiency on three stop codons of UAG, UAA and UGA. By using the dual luciferase reporter system to accurately quantify the read-through efficiency of the suppressor tRNAs, we found that the highest read-through efficiency of stRNAGln-UAG on the premature termination codon UAG of the dual luciferase reporter system was 44.7%±1.36%, the highest read-through efficiency of stRNAGln-UAA on the premature termination codon UAA of the dual luciferase reporter system was 30.95%±1.358%, the highest read-through efficiency of stRNAArg-UGA on the premature termination codon UGA of the dual luciferase reporter system was 22.55%±1.39%, all are far higher than the read-through efficiency reported in the literature (Ramesh Koukuntla. et al. J Gene Med, 2013, 15, 93-101.); (6) The suppressor tRNA of step (1) was transfected into tumor cell lines A549 and DU145; the protein was extracted after culturing for 48 hours to prove the restoration of expression of STK11 protein and the full-length EPHB2 protein in tumor cell lines A549 and DU145 by western blot.

The principle of reading through a nonsense mutation by a suppressor tRNA is as follows: (1) In the normal translation process of a cell, the premature termination codon is recognized by the first class peptide chain release factor eRF1, while the normal tRNA cannot recognize the stop codon. eRF3 is a GTPase which relies on the ribosome and the first class peptide chain release factor, cooperates with eRF1 to promote release of the peptide chain from the ribosome, and the termination of the translation process (Zhouravleva, G. et al. EMBO J, 1995, 14, 4065-72.). The constructed suppressor tRNAs are obtained by engineering the anticodon loops of normal tRNAs, and their anti-codon loops can be completely complementary to the stop codons UAG, UAA, UGA, and compete with eRF1 to recognize the premature termination codons. The tRNAs with changed anticodon loops can still carry the corresponding amino acids. Therefore, the suppressor tRNAs insert amino acids at the positions of the premature termination codons so that the translation process continues, and the nonsense mutations are read through; (2) The constructed suppressor tRNAs are ligated to a 7sk promoter at 5' end, and are capable of initiating sufficient expression of suppressor tRNAs in mammalian cells, and ultimately restore protein expression.

In a specific embodiment of the invention, the rapid construction of any suppressor tRNA carrying a 7sk promoter is achieved using the SOE PCR method. The principle is that the suppressor tRNA is only a single base substitution of a normal tRNA, and the size is generally about 80 bp, and the length is small. It is possible to design a partially complementary pair of upstream and downstream primers for direct PCR synthesis, and the synthesized suppressor tRNA is subjected to the second step of PCR and ligated to the 3' end of the 7sk promoter. Specifically, upstream and downstream primers covering all suppressor tRNAs and partially complementary were designed, and the remaining primers were designed according to the conventional method of SOE PCR. Suppressor tRNAs and the 7sk promoter sequence were synthesized respectively in the first step of PCR, and the suppressor tRNAs were ligated to the 7sk promoter in the second step of PCR to achieve the synthesis of the suppressor tRNAs with the 7sk promoter.

In a specific embodiment of the invention, Renila luciferase and Firefly enzyme dual luciferase reporter genes pGL4-2luc-TAG; pGL4-2luc-TAA; pGL4-2luc-TGA respectively comprising stop codons UAG, UAA, UGA therein were used to detect the read-through efficiency of different suppressor tRNAs. That is, suppressor tRNAs and the corresponding dual luciferase reporter genes were transfected into 293T cells, and the fluorescence readout values of Firefly and Renila were measured respectively, and the difference in the read-through efficiency was determined according to the relative fluorescence value of Firefly relative to Renila. At the same time, the amino acid codon at position 39 of GFP fluorescent gene was point mutated to the three premature termination codons of UAG, UAA and UGA respectively by point mutation technology to obtain pcDNA3.1-GFP-39TAG; pcDNA3.1-GFP-39TAA; pcDNA3.1-GFP-39TGA vectors. The read-through efficiency of the suppressor tRNAs was determined by detecting the GFP fluorescence intensity in the 293T cells. Finally, Amber suppressor tRNA (Gln), Ocher suppressor tRNA (Gln) and Opal suppressor tRNA (Arg) were determined as tRNAs having the highest efficiency for reading through UAG, UAA and UGA.

In a specific embodiment of the invention, the suppressor tRNAs were applied to restore the expression of nonsense mutant proteins associated with human hereditary diseases. According to the positions of nonsense mutations in human DMD diseases, point mutations were performed at the corresponding positions of the normal Dp71b sequence to mimic the DMD gene sequences in human DMD diseases. Dp71b3115TAG comprising the premature termination codon UAG was mutated to c.9346C>T; Dp71b3216TAA comprising the premature termination codon UAA was mutated to c.9651C>A; and Dp71b3112TGA comprising the premature termination codon UGA was mutated to c.9337C>T. The mutated Dp71b protein plasmids were co-transfected into 293T cells with different suppressor tRNAs to restore the expression of Dp71b.

In a specific embodiment of the invention, a suppressor tRNA was used to read through a nonsense mutation site of a tumor suppressor gene in a tumor cell. Bjmu-stRNAGln-UAG was transfected into tumor cell lines A549 and DU145 (the nonsense mutation c.109C>T, p.Q37X occurred in STK11 on human lung cancer cell A 549 genome is the stop codon UAG; the nonsense mutation c.2167C>T, p.Q723X occurred in EPHB2 gene on the human prostate cancer cell DU 145 genome is the stop codon UAG). The protein was extracted after adding non-natural amino acids and culturing for 48 hours. The restoration of the expression of the full-length STK11 protein and the full-length EPHB2 protein in tumor cell lines A549 and DU145 by the genetic codon expansion technology was proved by western blot.

More specifically, the present invention provides

1. An expression vector comprising 19 suppressor tRNAs with a 7sk promoter, the 19 suppressor tRNAs being Bjmu-stRNAGln-UAG; Bjmu-stRNATyr-UAG; Bjmu-stRNALys-UAG; Bjmu-stRNALeu-UAG; Bjmu-stRNAGlu-UAG; Bjmu-stRNATrp-UAG; Bjmu-stRNAArg-UGA; Bjmu-stRNAGln-UGA; Bjmu-stRNATrp-UGA; Bjmu-stRNAGly-UGA; Bjmu-stRNACys-UGA; Bjmu-stRNALeu-UGA; Bjmu-stRNASer-UGA; Bjmu-stRNAGln-UAA; Bjmu-stRNATyr-UAA; Bjmu-stRNALys-UAA; Bjmu-stRNAGlu-UAA; Bjmu-stRNALeu-UAA; Bjmu-stRNASer-UAA, which can achieve overexpression of different suppressor tRNAs.

2. The double luciferase reporter gene pGL4-2luc-TAG; pGL4-2luc-TAA; pGL4-2luc-TGA comprising a stop codon, which has the sequence of SEQ ID NO:22. The read-through efficiency of the suppressor tRNAs can be reflected by determining the fluorescence intensity of Firely relative to Renila of this gene.

3. The vectors pcDNA3.1-GFP-39TAG; pcDNA3.1-GFP-39TAA; pcDNA3.1-GFP-39TGA carrying green fluorescent protein reporter genes in which position Tyr39 was mutated to UAG, UAA, UGA respectively. Said vector can reflect the read-through efficiency by the fluorescence intensity. The non-mutated sequence is shown in SEQ ID NO:21.

4. Dp71b protein plasmids Dp71b3115TAG; Dp71b3216TAA; Dp71b3112TGA comprising the premature termination codons UAG, UAA, UGA. The non-mutated Dp71b sequence is shown in SEQ ID NO:23.

b: Schematic diagram of the read-through of the PTC by the suppressor tRNA. The anticodon loop of the tRNA carrying an amino acid is completely complementary to the premature termination codon and read through the PTC.

c: A 7sk promoter is ligated to the 5' end of the suppressor tRNA by SOE PCR method;

d: The suppressor tRNA was cut by both BamHI and Bgl II enzymes. Bjmu vector was cut by BamHI enzyme alone, and the product of the cutting is ligated to obtain the Bjmu vector comprising the 7sk-suppressor tRNA.

Figure 1:
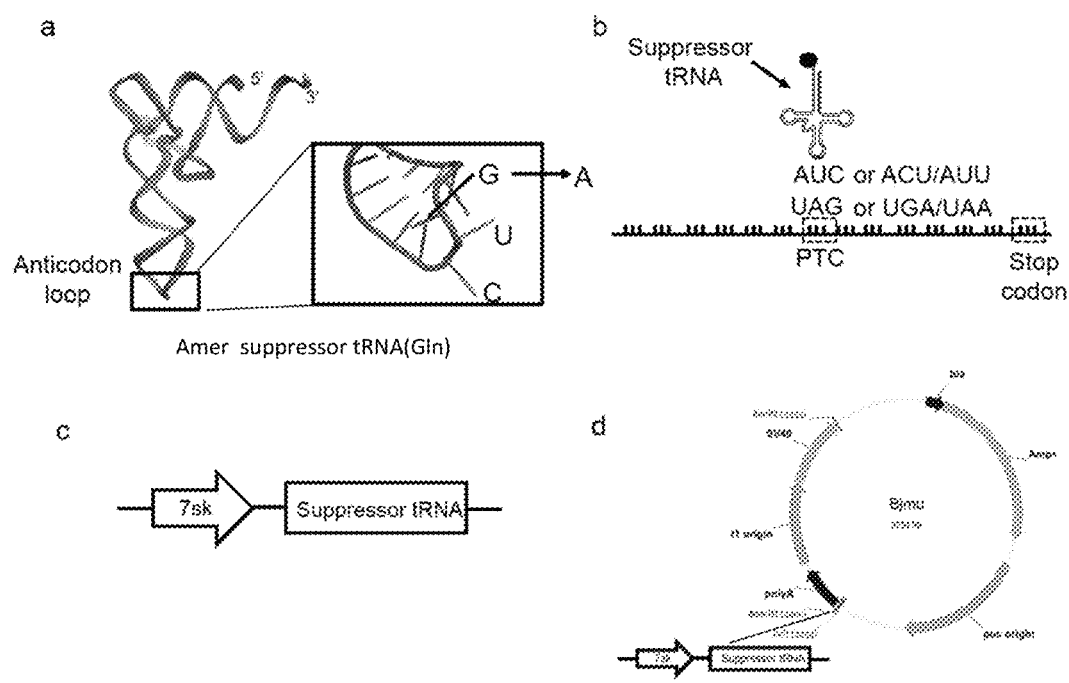
FIG. 1: Construction of a suppressor tRNA plasmid a: The synthesis of the suppressor tRNA by engineering the anticodon loop of a normal tRNA.
Figure 2:
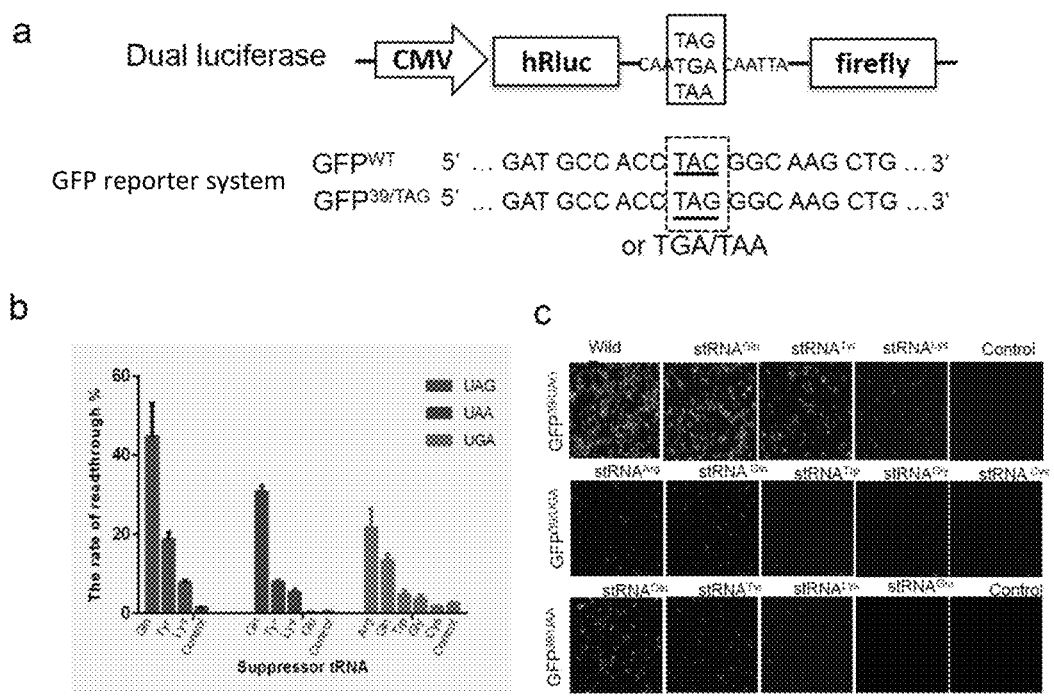

FIG. 2: Detection of the read-through efficiency of a suppressor tRNA with dual luciferase reporter gene and GFP reporter gene.

a: Construction of dual luciferase reporter gene and GFP reporter gene. A linker comprising a premature termination codon is linked between two luciferases. The amino acid at position 39 of the wild type GFP gene is mutated to a premature termination codon.

b: Detection of the read-through efficiency of different suppressor tRNAs with dual luciferase reporter gene. Different suppressor tRNAs have different read-through efficiency. Amber suppressor tRNA (Gln), Ocher suppressor tRNA (Gln) and Opal suppressor tRNA (Arg) have the highest efficiency for reading through UAG, UAA and UGA respectively.

c: The detection of the read-through efficiency of different suppressor tRNAs by fluorescence intensity of GFP reporter gene further demonstrates that the suppressor tRNAs have different read-through efficiency.

Figure 3:
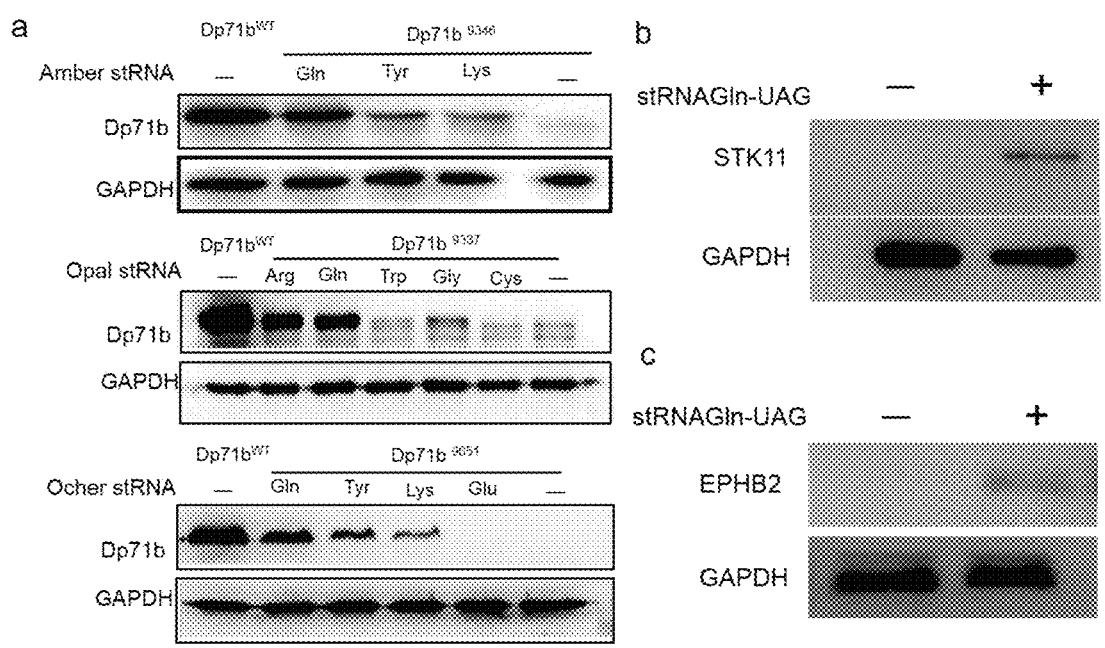

FIG. 3: Suppressor tRNAs restore the expression of nonsense mutant proteins in PTC diseases and in tumor cells.

a: Suppressor tRNAs can restore the expression of Dp71b protein, but the efficiency for the restoration is different;

b: The expression of STK11 protein is restored in A549 by transfecting the suppressor tRNAGln-UAG;

c: The expression of STK11 protein is restored in DU145 by transfecting the suppressor tRNAGln-UAG.

In order to better understand the present invention, the inventors have described and illustrated the specific experiments by the Examples, which are intended to illustrate and not to limit the scope of the present invention. Any variations or embodiments equivalent to the invention are included in the invention.

EXAMPLE 1: OBTAINMENT OF 19 SUPPRESSOR TRNAS

Identification of 19 Suppressor tRNAs

According to the characteristics of mutations of human PTC diseases, the sequences of tRNAs corresponding to 19 amino acid codons which can have nonsense mutations were determined. The anticodon loops of the tRNAs were changed to obtain the suppressor tRNAs which were completely complementary to the premature termination codons. The 19 suppressor tRNAs were respectively, Amber suppressor tRNA: suppressor tRNA (Gln/UAG), suppressor tRNA (Tyr/UAG), suppressor tRNA (Lys/UAG), suppressor tRNA (Leu/UAG), suppressor tRNA (Glu/UAG), suppressor tRNA (Trp/UAG); Opal suppressor tRNA: suppressor tRNA (Arg/UGA), suppressor tRNA (Gln/UGA), suppressor tRNA (Trp/UGA), suppressor tRNA (Gly/UGA), suppressor tRNA (Cys/UGA), suppressor tRNA (Leu/UGA), suppressor tRNA (Ser/UGA); Ocher suppressor tRNA: suppressor tRNA (Gln/UAA), suppressor tRNA (Tyr/UAA), suppressor tRNA (Lys/UAA), suppressor tRNA (Glu/UAA), suppressor tRNA (Leu/UAA), suppressor tRNA (Ser/UAA).

The Design of SOE PCR Primers and Point Mutation Primers

According to the determined sequences of the 19 suppressor tRNAs, 19 suppressor tRNAs having a 7sk promoter ligated at the 5' end were synthesized, wherein three suppressor tRNAs, suppressor tRNA (Gln/UAG), suppressor tRNA (Tyr/UAG) and suppressor tRNA (Lys/UAG) were obtained by total sequence synthesis, and the remaining 13 suppressor tRNAs were synthesized by SOE PCR and ligated to the 7sk promoter at the 5' end, and three were obtained by point mutations of the resulted suppressor tRNAs.

TABLE 1

| 7SK PROMOTER SEQUENCE | | |
|---|---|---|
| name | Sequence (5'-3' direction) | |
| 7sk | CTGCAGTATTTAGCATGCCCCACCCATCT GCAAGGCATTCTGGATAGTGTCAAAACAG CCGGAAATCAAGTCCGTTTATCTCAAACTT TAGCATTTTGGGAATAAATGATATTTGCTA TGCTGGTTAAATTAGATTTTAGTTAAATTT CCTGCTGAAGCTCTAGTACGATAAGTAACT TGACCTAAGTGTAAAGTTGAGATTTCCTTC GAGTTTATATAGCTTGTGCGCCGCCTGGG TACCTC | SEQ ID NO. 24 |

TABLE 2

| SOE PCR PRIMER SEQUENCES | | |
|---|---|---|
| Name of the primer | Sequence (5'-3' direction) | |
| 7sk-for | CGGGATCCCTGCAGTATTTAGCATG | SEQ ID NO. 25 |
| 7sk-Arg-UGA-rev | ATCCATTAGGCCACGTGGTCCGAGGTACCCAGGCGGCG | SEQ ID NO. 26 |
| UGA-Arg-for | CGCCGCCTGGGTACCTCGGACCACGTGGCCTAATGGATAAGGCGTCTGACTTCAGATCAGA | SEQ ID NO. 27 |
| UGA-Arg-rev | GAAGATCTAAAAAAACCACGAAGGGATTCGAACCCTCAATCTTCTGATCTGAAGTCAGACGC | SEQ ID NO. 28 |
| Arg(UGA)-rev | GAAGATCTAAAAAAACCACGAAGGG | SEQ ID NO. 29 |
| 7sk-Trp-UGA-rev | TTGCGCCACGAGGTCGAGGTACCCAGGCG | SEQ ID NO. 30 |
| UGA-Trp-for | CGCCGCCTGGGTACCTCGACCTCGTGGCGCAACGGCAGCGCGTCTGACTTCAGATCAGAAG | SEQ ID NO. 31 |
| UGA-Trp-rev | GAAGATCTAAAAAGACCCCGACGTGATTTGAACACGCAACCTTCTGATCTGAAGTCAGACGC | SEQ ID NO. 32 |
| Trp(UGA)-rev | GAAGATCTAAAAAGACCCCGACGTG | SEQ ID NO. 33 |
| 7sk-Gly-UGA-rev | TAACCACTATACCACCAACGCGAGGTACCCAGGCGGCG | SEQ ID NO. 34 |
| UGA-Gly-for | CGCCGCCTGGGTACCTCGCGTTGGTGGTATAGTGGTTAGCATAGCTGCCTTCAAAGCAGT | SEQ ID NO. 35 |
| UGA-Gly-rev | GAAGATCTAAAAATGCGTTGGCCGGGAATCGAACCCGGGTCAACTGCTTTGAAGGCAGC | SEQ ID NO. 36 |
| Gly(UGA)-rev | GAAGATCTAAAAATGCGTTGGCCG | SEQ ID NO. 37 |
| 7sk-Cys-UGA-rev | TGAGCCCTACCCCCGAGGTACCCAGGCGG | SEQ ID NO. 38 |
| UGA-Cys-for | CGCCGCCTGGGTACCTCGGGGGTAGGGCTCAGGGATAGAGCATTTGACTTCAGATCAAG | SEQ ID NO. 39 |
| UGA-Cys-rev | GAAGATCTAAAAGGGGCACCTAGATTCGAACCGGGGACCTCTTGATCTGAAGTCAAAT | SEQ ID NO. 40 |
| Cys(UGA)-rev | GAAGATCTAAAAGGGGCACC | SEQ ID NO. 41 |
| 7sk-UGA-Leu-rev | GCTCTGCCATCTTAACGAGGTACCCAGGCGGC | SEQ ID NO. 42 |
| UGA-Leu-for | GCCGCCTGGGTACCTCGTTAAGATGGCAGAGCCCGGCAATTGCATAAGACTTCAAACTTTAT | SEQ ID NO. 43 |
| UGA-Leu-rev | GAAGATCTAAAAAGTTAATGAGAGGAGTTGAACCTCTGATTATAAAGTTTGAAGTCTTATGC | SEQ ID NO. 44 |
| UGA-Leu-rev(2) | GAAGATCTAAAAAGTTAATGAGAGG | SEQ ID NO. 45 |
| 7sk-UGA-Ser-rev | TTAACCACTCGGCCACGACTACGAGGTACCCAGGCGGC | SEQ ID NO. 46 |
| UGA-Ser-for | GCGCCGCCTGGGTACCTCGTAGTCGTGGCCGAGTGGTTAAGGCGATGGACTTCAAATCCATTGGGGTT | SEQ ID NO. 47 |
| UGA-Ser-rev | GAAGATCTAAAAACGTAGTCGGCAGGATTCGAACCTGCGCGGGGAAACCCCAATGGATTTGAAGTCC | SEQ ID NO. 48 |
| UGA-Ser-rev(2) | GAAGATCTAAAAACGTAGTCGGCAGG | SEQ ID NO. 49 |
| 7sk-Glu-UAA-rev | ACTAGACCACCAGGGAGAGGTACCCAGGCG | SEQ ID NO. 50 |
| UAA-Glu-for | CGCCGCCTGGGTACCTCTCCCTGGTGGTCTAGTGGCTAGGATTCGGCGCTTTAACCGCC | SEQ ID NO. 51 |
| UAA-Glu-rev | GAAGATCTAAAAAATTCCTGGCCGGGAATCGAACCCGGGGCGCGGCGGTTAAAGCGCCG | SEQ ID NO. 52 |
| Glu-UAA-rev | GAAGATCTAAAAAATTCCTGGCCGG | SEQ ID NO. 53 |
| 7sk-Gln-UAA-rev | ATTACACCATGGGACCGAGGTACCCAGGCG | SEQ ID NO. 54 |
| UAA-Gln-for | CGCCGCCTGGGTACCTCGGTCCCATGGTGTAATGGTTAGCACTCTGGACTTTAAATCCA | SEQ ID NO. 55 |

TABLE 2-continued

SOE PCR PRIMER SEQUENCES

| Name of the primer | Sequence (5'-3' direction) | |
|---|---|---|
| UAA-Gln-rev | GAAGATCTAAAAAAGGTCCCACCGAGATTTGAACTCGGATCGCTGGATTTAAAGTCCAG | SEQ ID NO. 56 |
| Gln-UAA-rev | GAAGATCTAAAAAAGGTCCCACCG | SEQ ID NO. 57 |
| 7sk-Lys-UAA-rev | ACTGAGCTATCCGGGCGAGGTACCCAGGCG | SEQ ID NO. 58 |
| UAA-Lys-for | CGCCGCCTGGGTACCTCGCCCGGATAGCTCAGTCGGTAGAGCATCAGACTTTAAATCTGA | SEQ ID NO. 59 |
| UAA-Lys-rev | GAAGATCTAAAAACGCCCGAACAGGGACTTGAACCCTGGACCCTCAGATTTAAAGTCTG | SEQ ID NO. 60 |
| Lys-UAA-rev | GAAGATCTAAAAACGCCCGAACAGG | SEQ ID NO. 61 |
| 7sk-UAA-Leu-rev | GCTCTGCCATCTTAACGAGGTACCCAGGCGGC | SEQ ID NO. 62 |
| UAA-Leu-for | GCGCCGCCTGGGTACCTCGTTAAGATGGCAGAGCCCGGCAATTGCATAAGACTTTAAACTTTA | SEQ ID NO. 63 |
| UAA-Leu-rev | GAAGATCTAAAAAGTTAATGAGAGGAGTTGAACCTCTGATTATAAAGTTTAAAGTCTTATGC | SEQ ID NO. 64 |
| UAA-Leu-rev(2) | GAAGATCTAAAAAGTTAATGAGAGGAG | SEQ ID NO. 65 |
| 7sk-UAA-Ser-rev | TCGGCCACGACTACGAGGTACCCAGGCGGC | SEQ ID NO. 66 |
| UAA-Ser-for | GCGCCGCCTGGGTACCTCGTAGTCGTGGCCGAGTGGTTAAGGCGATGGACTTTAAATCCATTGGGGTT | SEQ ID NO. 67 |
| UAA-Ser-rev | GAAGATCTAAAAACGTAGTCGGCAGGATTCGAACCTGCGCGGGGAAACCCCAATGGATTTAAAGTCC | SEQ ID NO. 68 |
| UAA-Ser-rev(2) | GAAGATCTAAAAACGTAGTCGGCAGG | SEQ ID NO. 69 |
| 7sk-UAG-Leu-rev | ACTCGGCCATCCTGACGAGGTACCCAGGCGGC | SEQ ID NO. 70 |
| UAG-Leu-for | GCCGCCTGGGTACCTCGTCAGGATGGCCGAGTGGTCTAAGGCGCCAGACTCTAGTTCTGGTCTCCA | SEQ ID NO. 71 |
| UAG-Leu-rev | GAAGATCTAAAAAGTCAGAAGTGGGATTCGAACCCACGCCTCCATTGGAGACCAGAACTAGAG | SEQ ID NO. 72 |
| UAG-Leu-rev(2) | GAAGATCTAAAAAGTCAGAAGTGGG | SEQ ID NO. 73 |
| 7sk-UAG-Glu-rev | ACTAGACCACCAGGGAGAGGTACCCAGGC | SEQ ID NO. 74 |
| UAG-Glu-for | CCGCCTGGGTACCTCTCCCTGGTGGTCTAGTGGTTAGGATTCGGCGCTCTAACCGCCGC | SEQ ID NO. 75 |
| UAG-Glu-rev | GAAGATCTAAAAATTCCCTGACCGGGAATCGAACCCGGGCCGCGGCGGTTAGAGCGCCGAAT | SEQ ID NO. 76 |
| UAG-Glu-rev(2) | GAAGATCTAAAAATTCCCTGACCGGG | SEQ ID NO. 77 |

TABLE 3

DESIGN OF POINT MUTATION PRIMERS FOR THE SUPPRESSOR TRNAS

| Name of the point mutation primer | Sequence (5'-3' direction) | |
|---|---|---|
| 7sk-Gln-UGA for | ctcggatcgctggatttgaagtccagagtgctaac | SEQ ID NO. 78 |
| 7sk-Gln-UGA rev | gttagcactctggacttcaaatccagcgatccgag | SEQ ID NO. 79 |
| 7sk-Tyr-UAA for | gcgacctaaggatctaaagtcctccgctctacc | SEQ ID NO. 80 |
| 7sk-Tyr-UAA rev | ggtagagcggaggactttagatccttaggtcgc | SEQ ID NO. 81 |
| 7sk-Trp-UAG-for | gcaacggcagcgcgtctgactctagatcagaaggt | SEQ ID NO. 82 |
| UAG-Trp-rev | accttctgatctagagtcagacgcgctgccgttgc | SEQ ID NO. 83 |

(3) Ligating the tRNA into Bjmu Vector

The suppressor tRNA was cut by both BamHI and Bgl II enzymes. Bjmu vector was cut by BamHI enzyme alone, and the product of the cutting is ligated to obtain the Bjmu vector comprising the 7sk-suppressor tRNA.

EXAMPLE 2: DETECTION OF READ-THROUGH EFFICIENCY OF 19 SUPPRESSOR TRNAS USING A DUAL FLUORESCEIN REPORTER GENE AND A POINT-MUTATED GFP REPORTER GENE (1) Construction of a GFP Reporter Gene Containing Premature Termination Codons Green fluorescent protein GFP is the most commonly used reporter gene and a powerful tool for indicating the insertion of non-natural amino acids. It consists of 238 amino acids and its gene sequence is represented by SEQ ID NO: 21.

The GFP sequence was inserted into the pcDNA3.1 commercial plasmid, and the amino acid codon at position 39 of the GFP fluorescent gene was mutated to three premature termination codons UAG, UAA and UGA respectively. Primers capable of mutating the codon encoding the amino acid into three stop codons respectively were designed, and the specific primers are shown in the following table.

TABLE 4

LIST OF GFP MUTATION PRIMERS

| | | |
|---|---|---|
| GFP-39-UAG-for | GGCGAGGGCGATGC CACCTAGGGCAAGC TGACCCTGAAGTTC | SEQ ID NO. 84 |
| GFP-39-UAG-for | GAACTTCAGGGTCA GCTTGCCCTAGGTG GCATCGCCCTCGCC | SEQ ID NO. 85 |
| GFP-39-UAA-for | GGCGAGGGCGATGC CACCTAAGGCAAGC TGACCCTGAAGTTC | SEQ ID NO. 86 |
| GFP-39-UAA-for | GAACTTCAGGGTCA GCTTGCCTTAGGTG GCATCGCCCTCGCC | SEQ ID NO. 87 |
| GFP-39-UAG-for | GGCGAGGGCGATGC CACCTGAGGCAAGC TGACCCTGAAGTTC | SEQ ID NO. 88 |
| GFP-39-UAG-for | GAACTTCAGGGTCA GCTTGCCTCAGGTG GCATCGCCCTCGCC | SEQ ID NO. 89 |

The expression plasmids (pcDNA3.1-GFP-39TAG, pcDNA3.1-GFP-39TAA and pcDNA3.1-GFP-39TGA) were constructed by using the wild-type GFP expression vector pcDNA3.1-GFP-WT as a template, mutating the amino acid codon at position 39 to three stop codons respectively with the site-directed mutagenesis kit (QuikChange® Lightning Site-Directed Mutagenesis Kits, Catalog #210518) according to the instructions. The mutation was verified to be successful by sequencing.

(2) Verification of the Read-Through Efficiency of the Suppressor tRNAs in 293T Cells by Transfecting Different Suppressor tRNA Plasmids and the Dual Luciferase Reporter Gene Respectively Suppressor tRNA vectors were mixed with the dual fluorescein reporter gene pGL4-2luc-TAG; pGL4-2luc-TAA; pGL4-2luc-TGA plasmids in a ratio of 1:2 according to the grouping of table 5, and then mixed with the transfection reagent megatrans1.0 in a ratio of 1:3. They were added together to 293T cells. After 6 hours, the solution was changed, luciferase substrate was added into the cell lysing solution, and fluorescence readings were detected. The result was shown in FIG. 2b. After adding the suppressor tRNAs, the full length active mutant firefly luciferase protein could be obtained. Finally, Amber suppressor tRNA (Gln), Ocher suppressor tRNA (Gln) and Opal suppressor tRNA (Arg) were determined as suppressor tRNAs having the highest efficiency for reading through UAG, UAA and UGA respectively.

TABLE 5

GROUPING OF DUAL LUCIFERASE REPORTER GENE TRANSFECTION PLASMIDS

| group | plasmids |
|---|---|
| 1 | Bjmu-stRNAGln-UAG and pGL4-2luc-TAG |
| 2 | Bjmu-stRNATyr-UAG and pGL4-2luc-TAG |
| 3 | Bjmu-stRNALys-UAG and pGL4-2luc-TAG |
| 4 | Bjmu-stRNALeu-UAG and pGL4-2luc-TAG |
| 5 | Bjmu-stRNAGlu-UAG and pGL4-2luc-TAG |
| 6 | Bjmu-stRNATrp-UAG and pGL4-2luc-TAG |
| 7 | Bjmu-stRNAArg-UGA and pGL4-2luc-TGA |
| 8 | Bjmu-stRNAGln-UGA and pGL4-2luc-TGA |
| 9 | Bjmu-stRNATrp-UGA and pGL4-2luc-TGA |
| 10 | Bjmu-stRNAGly-UGA and pGL4-2luc-TGA |
| 11 | Bjmu-stRNACys-UGA and pGL4-2luc-TGA |
| 12 | Bjmu-stRNALeu-UGA and pGL4-2luc-TGA |
| 13 | Bjmu-stRNASer-UGA and pGL4-2luc-TGA |
| 14 | Bjmu-stRNAGln-UAA and pGL4-2luc-TAA |
| 15 | Bjmu-stRNATyr-UAA and pGL4-2luc-TAA |
| 16 | Bjmu-stRNALys-UAA and pGL4-2luc-TAA |
| 17 | Bjmu-stRNAGlu-UAA and pGL4-2luc-TAA |
| 18 | Bjmu-stRNALeu-UAA and pGL4-2luc-TAA |
| 19 | Bjmu-stRNASer-UAA and pGL4-2luc-TAA |

(3) Verification of the Read-Through Efficiency of the Suppressor tRNAs in 293T Cells by Transfecting 19 Suppressor tRNAs and pcDNA3.1-GFP Plasmid The pcDNA3.1-GFP-39TXX obtained in step 1 of Example 2 and the 19 suppressor tRNA plasmids of step 3 of Example 1 were transfected into 293T cells according to the grouping of table 6 and the way of transfection of step 2 of Example 2. After 48 hours, green fluorescence was observed by fluorescence microscopy, and the result was shown in FIG. 2c. Finally, Amber suppressor tRNA (Gln), Ocher suppressor tRNA (Gln) and Opal suppressor tRNA (Arg) were further verified as suppressor tRNAs having the highest efficiency for reading through UAG, UAA and UGA respectively.

TABLE 6

GROUPING OF GFP REPORTER GENE TRANSFECTION PLASMIDS

| group | plasmids |
|---|---|
| 1 | Bjmu-stRNAGln-UAG and pcDNA3.1-GFP-39TAG |
| 2 | Bjmu-stRNATyr-UAG and pcDNA3.1-GFP-39TAG |
| 3 | Bjmu-stRNALys-UAG and pcDNA3.1-GFP-39TAG |
| 4 | Bjmu-stRNALeu-UAG and pcDNA3.1-GFP-39TAG |
| 5 | Bjmu-stRNAGlu-UAG and pcDNA3.1-GFP-39TAG |
| 6 | Bjmu-stRNATrp-UAG and pcDNA3.1-GFP-39TAG |
| 7 | Bjmu-stRNAArg-UGA and pcDNA3.1-GFP-39TGA |
| 8 | Bjmu-stRNAGln-UGA and pcDNA3.1-GFP-39TGA |
| 9 | Bjmu-stRNATrp-UGA and pcDNA3.1-GFP-39TGA |
| 10 | Bjmu-stRNAGly-UGA and pcDNA3.1-GFP-39TGA |
| 11 | Bjmu-stRNACys-UGA and pcDNA3.1-GFP-39TGA |
| 12 | Bjmu-stRNALeu-UGA and pcDNA3.1-GFP-39TGA |

TABLE 6-continued

GROUPING OF GFP REPORTER GENE TRANSFECTION PLASMIDS

| group | plasmids |
|---|---|
| 13 | Bjmu-stRNASer-UGA and pcDNA3.1-GFP-39TGA |
| 14 | Bjmu-stRNAGln-UAA and pcDNA3.1-GFP-39TAA |
| 15 | Bjmu-stRNATyr-UAA and pcDNA3.1-GFP-39TAA |
| 16 | Bjmu-stRNALys-UAA and pcDNA3.1-GFP-39TAA |
| 17 | Bjmu-stRNAGlu-UAA and pcDNA3.1-GFP-39TAA |
| 18 | Bjmu-stRNALeu-UAA and pcDNA3.1-GFP-39TAA |
| 19 | Bjmu-stRNASer-UAA and pcDNA3.1-GFP-39TAA |

EXAMPLE 3: READING THROUGH THE DISEASE PROTEIN DYSTROPHIN IN THE 293T CELL LINE (1) Construction of the Dp71b Mutant Plasmids Containing the Premature Termination Codon UAG, UAA, UGA The sequence of the isoform of the Dystrophin protein, Dp71b, is shown in SEQ ID NO: 23. The inventors performed point mutations on the wild-type Dp71b sequence according to the sites of nonsense mutations in Duchenne muscular dystrophy patients, and introduced premature termination codons at different positions to construct Dp71b3115TAG comprising the premature termination codon UAG (mutated to c.9346C>T), Dp71b3216TAA comprising the premature termination codon UAA (mutated to c.9651C>A), and Dp71b3112TGA comprising the premature termination codon UGA (mutated to c.9337C>T). The mutations were verified to be successful by sequencing.

(2) Reading Through the Disease Protein Dystrophin in the 293T Cell Line

The Dp71b3115TAG, Dp71b3216TAA and Dp71b3112TGA obtained in step 1 of Example 3 and the corresponding suppressor tRNAs were transfected into 293T cells according to the way of transfection of step 2 of Example 2. After cells were cultured for 48 hours, the protein was extracted. The production of the full-length dystrophin protein was detected by Western blot (the primary antibody was anti-dystrophin, which was a C-terminal antibody of an anti-dystrophin protein, catalog No. 12715-1-AP), as shown in FIG. 3a. It was proved that the suppressor tRNAs could read through different types of premature termination codons and restore the expression of disease proteins.

EXAMPLE 4: SUPPRESSOR TRNAS READ THROUGH PREMATURE TERMINATION CODON IN THE GENOME OF A TUMOR CELL LINE

According to the literature, STK11 on human lung cancer cell A 549 genome has a nonsense mutation, c.109C>T, p. Q37X, which is an amber stop codon UAG; EPHB2 gene on human prostate cancer cell DU 145 genome has a nonsense mutation, c.2167C>T, p. Q723X, which is an amber stop codon UAG.

The Bjmu-stRNAGln-UAG plasmid was mixed with the transfection reagent megatrans1.0 in a ratio of 1:3, and was transfected into A 549 and DU145 cells respectively. After 6 hours, the solution was changed. After the cells were cultured in an incubator at 37° C., 5% CO2 for 48 hours, the protein was extracted. The production of the full-length STK11 and EPHB2 proteins was detected by Western blot (the primary antibodies were anti-STK11 and anti-EPHB2 respectively), as shown in FIGS. 3b and 3c. It was verified that the suppressor tRNAs could read through the premature termination codon on the endogenous genome to restore the expression of the tumor suppressor gene proteins.

What have been described above are only some embodiments of the invention. It will be apparent to those skilled in the art that various variations and modifications can be made without departing from the spirit and scope of the invention, which all fall into the protection scope of the present invention.

The invention claimed is:

1. A suppressor tRNA, wherein the suppressor tRNA is selected from the group consisting of the suppressor tRNAs set forth in SEQ ID NOs: 1-19.

2. The suppressor tRNA of claim 1 in a plasmid, a vector or a kit.

3. The kit of claim 2, wherein the kit comprises a suppressor tRNA having the sequence set forth in any one of SEQ ID NOs: 1-19.

4. The kit of claim 3, wherein the kit comprises the Amber suppressor tRNA (Gln) corresponding to SEQ ID NO: 1; the Ocher suppressor tRNA (Gln) corresponding to SEQ ID NO: 14; or the Opal suppressor tRNA (Arg) corresponding to SEQ ID NO: 7.

* * * * *

SEQUENCE LISTING

<160> NUMBER OF SEQ ID NOS: 89

<210> SEQ ID NO 1
<211> LENGTH: 332
<212> TYPE: DNA
<213> ORGANISM: Artificial Sequence
<220> FEATURE:
<223> OTHER INFORMATION: Synthetic Polynucleotide

<400> SEQUENCE: 1

```
ggatccctgc agtatttagc atgccccacc catctgcaag gcattctgga tagtgtcaaa      60
acagccggaa atcaagtccg tttatctcaa actttagcat tttgggaata aatgatattt     120
gctatgctgg ttaaattaga ttttagttaa atttcctgct gaagctctag tacgataagt     180
aacttgacct aagtgtaaag ttgagatttc cttcaggttt atatagcttg tgcgccgcct     240
gggtacctcg gttccatggt gtaatggtta gcactctgga ctctaaatcc agcgatccga     300
gttcaaatct cggtggaacc tttttagat ct                                    332
```

<210> SEQ ID NO 2
<211> LENGTH: 337
<212> TYPE: DNA
<213> ORGANISM: Artificial Sequence

```
<220> FEATURE:
<223> OTHER INFORMATION: Synthetic Polynucleotide

<400> SEQUENCE: 2
cgggatccct gcagtattta gcatgcccca cccatctgca aggcattctg gatagtgtca      60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt tccttcaggt ttatatagct tgtgcgccgc     240
ctgggtacct cccttcgata gctcagctgg tagagcggag gactctagat ccttaggtcg     300
ctggttcaat tccggctcga aggattttta gatcttc                              337

<210> SEQ ID NO 3
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 3
cgggatccct gcagtattta gcatgcccca cccatctgca aggcattctg gatagtgtca      60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt tccttcaggt ttatatagct tgtgcgccgc     240
ctgggtacct cgcccggcta gctcagtcgg tagagcatga gactctaaat ctcagggtcg     300
tgggttcgag ccccacgttg ggcgttttta gatcttc                              337

<210> SEQ ID NO 4
<211> LENGTH: 346
<212> TYPE: DNA
<213> ORGANISM: Artificial Sequence
<220> FEATURE:
<223> OTHER INFORMATION: Synthetic Polynucleotide

<400> SEQUENCE: 4
cgggatccct gcagtattta gcatgcccca cccatctgca aggcattctg gatagtgtca      60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt tccttcaggt ttatatagct tgtgcgccgc     240
ctgggtacct cgtcaggatg gccgagtggt ctaaggcgcc agactctagt tctggtctcc     300
aatggaggcg tgggttcgaa tcccacttct gactttttag atcttc                    346

<210> SEQ ID NO 5
<211> LENGTH: 330
<212> TYPE: DNA
<213> ORGANISM: Artificial Sequence
<220> FEATURE:
<223> OTHER INFORMATION: Synthetic Polynucleotide

<400> SEQUENCE: 5
cgggatccct gcagtattta gcatgcccca cccatctgca aggcattctg gatagtgtca      60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt tccttcaggt ttatatagct tgtgcgccgc     240
```

```
ctgggtacct ctccctggtg gtctagtggt taggattcgg cgctctaacc gccgcggccc    300
gggttcgatt cccggtcagg gaatttttag                                     330
```

<210> SEQ ID NO 6
<211> LENGTH: 335
<212> TYPE: DNA
<213> ORGANISM: Artificial Sequence
<220> FEATURE:
<223> OTHER INFORMATION: Synthetic Polynucleotide

<400> SEQUENCE: 6

```
cgggatccct gcagtattta gcatgcccca cccatctgca aggcattctg gatagtgtca     60
aaacagccgg aaatcaagtc cgtttatctc aaactttagc attttgggaa taaatgatat    120
ttgctatgct ggttaaatta gattttagtt aaatttcctg ctgaagctct agtacgataa    180
gtaacttgac ctaagtgtaa agttgagatt tccttcaggt ttatatagct tgtgcgccgc    240
ctgggtacct cgacctcgtg gcgcaacggc agcgcgtctg actctagatc agaaggttgc    300
gtgttcaaat cacgtcgggg tcttttaga tcttc                                335
```

<210> SEQ ID NO 7
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 7

```
cgggatccct gcagtattta gcatgcccca cccatctgca aggcattctg gatagtgtca     60
aaacagccgg aaatcaagtc cgtttatctc aaactttagc attttgggaa taaatgatat    120
ttgctatgct ggttaaatta gattttagtt aaatttcctg ctgaagctct agtacgataa    180
gtaacttgac ctaagtgtaa agttgagatt tccttcaggt ttatatagct tgtgcgccgc    240
ctgggtacct cggaccacgt ggcctaatgg ataaggcgtc tgacttcaga tcagaagatt    300
gagggttcga atcccttcgt ggttttttta gatcttc                             337
```

<210> SEQ ID NO 8
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 8

```
cgggatccct gcagtattta gcatgcccca cccatctgca aggcattctg gatagtgtca     60
aaacagccgg aaatcaagtc cgtttatctc aaactttagc attttgggaa taaatgatat    120
ttgctatgct ggttaaatta gattttagtt aaatttcctg ctgaagctct agtacgataa    180
gtaacttgac ctaagtgtaa agttgagatt tccttcaggt ttatatagct tgtgcgccgc    240
ctgggtacct cggtcccatg gtgtaatggt tagcactctg gacttcaaat ccagcgatcc    300
gagttcaaat ctcggtggga ccttttttag atcttc                              336
```

<210> SEQ ID NO 9
<211> LENGTH: 335
<212> TYPE: DNA
<213> ORGANISM: Artificial Sequence
<220> FEATURE:
<223> OTHER INFORMATION: Synthetic Polynucleotide

<400> SEQUENCE: 9

```
cgggatccct gcagtattta gcatgcccca cccatctgca aggcattctg gatagtgtca      60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt ccttcaggt ttatatagct tgtgcgccgc      240
ctgggtacct cgacctcgtg gcgcaacggc agcgcgtctg acttcagatc agaaggttgc    300
gtgttcaaat cacgtcgggg tcttttttaga tcttc                               335
```

<210> SEQ ID NO 10
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 10

```
cgggatccct gcagtattta gcatgcccca cccatctgca aggcattctg gatagtgtca      60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt ccttcaggt ttatatagct tgtgcgccgc      240
ctgggtacct cgcgttggtg gtatagtggt tagcatagct gccttcaaag cagttgaccc    300
gggttcgatt cccggccaac gcattttag atcttc                                336
```

<210> SEQ ID NO 11
<211> LENGTH: 335
<212> TYPE: DNA
<213> ORGANISM: Artificial Sequence
<220> FEATURE:
<223> OTHER INFORMATION: Synthetic Polynucleotide

<400> SEQUENCE: 11

```
cgggatccct gcagtattta gcatgcccca cccatctgca aggcattctg gatagtgtca      60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt ccttcaggt ttatatagct tgtgcgccgc      240
ctgggtacct cggggtagg gctcagggat agagcatttg acttcagatc aagaggtccc     300
cggttcgaat ctaggtgccc cctttttaga tcttc                                335
```

<210> SEQ ID NO 12
<211> LENGTH: 338
<212> TYPE: DNA
<213> ORGANISM: Artificial Sequence
<220> FEATURE:
<223> OTHER INFORMATION: Synthetic Polynucleotide

<400> SEQUENCE: 12

```
cgggatccct gcagtattta gcatgcccca cccatctgca aggcattctg gatagtgtca      60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt ccttcaggt ttatatagct tgtgcgccgc      240
ctgggtacct cgttaagatg gcagagcccg gcaattgcat aagacttcaa actttataat   300
cagaggttca actcctctca ttaacttttt agatcttc                             338
```

```
<210> SEQ ID NO 13
<211> LENGTH: 346
<212> TYPE: DNA
<213> ORGANISM: Artificial Sequence
<220> FEATURE:
<223> OTHER INFORMATION: Synthetic Polynucleotide

<400> SEQUENCE: 13
cgggatccct gcagtattta gcatgcccca cccatctgca aggcattctg gatagtgtca      60
aaacagccgg aaatcaagtc cgtttatctc aaactttagc attttgggaa taaatgatat    120
ttgctatgct ggttaaatta gattttagtt aaatttcctg ctgaagctct agtacgataa    180
gtaacttgac ctaagtgtaa agttgagatt tccttcaggt ttatatagct tgtgcgccgc    240
ctgggtacct cgtagtcgtg gccgagtggt taaggcgatg gacttcaaat ccattggggt    300
ttccccgcgc aggttcgaat cctgccgact acgttttag atcttc                    346

<210> SEQ ID NO 14
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 14
cgggatccct gcagtattta gcatgcccca cccatctgca aggcattctg gatagtgtca      60
aaacagccgg aaatcaagtc cgtttatctc aaactttagc attttgggaa taaatgatat    120
ttgctatgct ggttaaatta gattttagtt aaatttcctg ctgaagctct agtacgataa    180
gtaacttgac ctaagtgtaa agttgagatt tccttcaggt ttatatagct tgtgcgccgc    240
ctgggtacct cggtcccatg gtgtaatggt tagcactctg gactttaaat ccagcgatcc    300
gagttcaaat ctcggtggga cctttttag atcttc                              336

<210> SEQ ID NO 15
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 15
cgggatccct gcagtattta gcatgcccca cccatctgca aggcattctg gatagtgtca      60
aaacagccgg aaatcaagtc cgtttatctc aaactttagc attttgggaa taaatgatat    120
ttgctatgct ggttaaatta gattttagtt aaatttcctg ctgaagctct agtacgataa    180
gtaacttgac ctaagtgtaa agttgagatt tccttcaggt ttatatagct tgtgcgccgc    240
ctgggtacct cccttcgata gctcagctgg tagagcggag gactttagat ccttaggtcg    300
ctggttcaat tccggctcga aggattttta gatcttc                            337

<210> SEQ ID NO 16
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 16
cgggatccct gcagtattta gcatgcccca cccatctgca aggcattctg gatagtgtca      60
aaacagccgg aaatcaagtc cgtttatctc aaactttagc attttgggaa taaatgatat    120
```

```
ttgctatgct ggttaaatta gattttagtt aaatttcctg ctgaagctct agtacgataa      180
gtaacttgac ctaagtgtaa agttgagatt tccttcaggt ttatatagct tgtgcgccgc      240
ctgggtacct cgcccggata gctcagtcgg tagagcatca gactttaaat ctgagggtcc      300
agggttcaag tccctgttcg ggcgttttta gatcttc                              337
```

<210> SEQ ID NO 17
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 17

```
cgggatccct gcagtattta gcatgcccca cccatctgca aggcattctg gatagtgtca       60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt tccttcaggt ttatatagct tgtgcgccgc     240
ctgggtacct ctccctggtg gtctagtggc taggattcgg cgctttaacc gccgcgcccc     300
gggttcgatt cccggccagg aatttttttag atcttc                              336
```

<210> SEQ ID NO 18
<211> LENGTH: 338
<212> TYPE: DNA
<213> ORGANISM: Artificial Sequence
<220> FEATURE:
<223> OTHER INFORMATION: Synthetic Polynucleotide

<400> SEQUENCE: 18

```
cgggatccct gcagtattta gcatgcccca cccatctgca aggcattctg gatagtgtca       60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt tccttcaggt ttatatagct tgtgcgccgc     240
ctgggtacct cgttaagatg gcagagcccg gcaattgcat aagactttaa actttataat     300
cagaggttca actcctctca ttaactttt agatcttc                              338
```

<210> SEQ ID NO 19
<211> LENGTH: 346
<212> TYPE: DNA
<213> ORGANISM: Artificial Sequence
<220> FEATURE:
<223> OTHER INFORMATION: Synthetic Polynucleotide

<400> SEQUENCE: 19

```
cgggatccct gcagtattta gcatgcccca cccatctgca aggcattctg gatagtgtca       60
aaacagccgg aaatcaagtc cgtttatctc aaactttagc attttgggaa taaatgatat     120
ttgctatgct ggttaaatta gattttagtt aaatttcctg ctgaagctct agtacgataa     180
gtaacttgac ctaagtgtaa agttgagatt tccttcaggt ttatatagct tgtgcgccgc     240
ctgggtacct cgtagtcgtg gccgagtggt taaggcgatg gactttaaat ccattggggt     300
ttccccgcgc aggttcgaat cctgccgact acgtttttag atcttc                   346
```

<210> SEQ ID NO 20
<211> LENGTH: 717
<212> TYPE: DNA
<213> ORGANISM: Artificial Sequence
<220> FEATURE:
<223> OTHER INFORMATION: Synthetic Polynucleotide

<400> SEQUENCE: 20

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgacctacgg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg      660
ctggagttcg tgaccgccgc cgggatcact ctcggcatgg acgagctgta caagtaa       717
```

<210> SEQ ID NO 21
<211> LENGTH: 720
<212> TYPE: DNA
<213> ORGANISM: Aequorea victoria

<400> SEQUENCE: 21

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 22
<211> LENGTH: 5976
<212> TYPE: DNA
<213> ORGANISM: Firefly

<400> SEQUENCE: 22

```
ggcctaactg gcctcaatat tggccattag ccatattatt cattggttat atagcataaa      60
tcaatattgg ctattggcca ttgcatacgt tgtatctata tcataatatg tacatttata     120
ttggctcatg tccaatatga ccgccatgtt ggcattgatt attgactagt tattaatagt     180
aatcaattac ggggtcatta gttcatagcc catatatgga gttccgcgtt acataactta     240
cggtaaatgg cccgcctggc tgaccgccca acgaccccg cccattgacg tcaataatga     300
```

```
cgtatgttcc catagtaacg ccaataggga ctttccattg acgtcaatgg gtggagtatt    360
tacggtaaac tgcccacttg gcagtacatc aagtgtatca tatgccaagt ccgcccccta    420
ttgacgtcaa tgacggtaaa tggcccgcct ggcattatgc ccagtacatg accttacggg    480
actttcctac ttggcagtac atctacgtat tagtcatcgc tattaccatg gtgatgcggt    540
tttggcagta caccaatggg cgtggatagc ggtttgactc acggggattt ccaagtctcc    600
accccattga cgtcaatggg agtttgtttt ggcaccaaaa tcaacgggac tttccaaaat    660
gtcgtaataa ccccgccccg ttgacgcaaa tgggcggtag gcgtgtacgg tgggaggtct    720
atataagcag agctcgttta gtgaaccgtc agatcactag aagctttatt gcggtagttt    780
atcacagtta aattgctaac gcagtcagtg gcctcggcg gccaagcttg gcaatccggt    840
actgttggta aagccaccat ggcttccaag gtgtacgacc ccgagcaacg caaacgcatg    900
atcactgggc ctcagtggtg ggctcgctgc aagcaaatga acgtgctgga ctccttcatc    960
aactactatg attccgagaa gcacgccgag aacgccgtga ttttctgca tggtaacgct    1020 gcctccagct acctgtggag gcacgtcgtg cctcacatca gcccgtggc tagatgcatc    1080 atccctgatc tgatcggaat gggtaagtcc ggcaagagcg ggaatggctc atatcgcctc    1140
ctggatcact acaagtacct caccgcttgg ttcgagctgc tgaaccttcc aaagaaaatc    1200
atctttgtgg gccacgactg gggggcttgt ctggcctttc actactccta cgagcaccaa    1260
gacaagatca aggccatcgt ccatgctgag agtgtcgtgg acgtgatcga gtcctgggac    1320
gagtggcctg acatcgagga ggatatcgcc ctgatcaaga gcgaagaggg cgagaaaatg    1380
gtgcttgaga ataacttctt cgtcgagacc atgctcccaa gcaagatcat gcggaaactg    1440
gagcctgagg agttcgctgc ctacctggag ccattcaagg agaagggcga ggttagacgg    1500
cctaccctct cctggcctcg cgagatccct ctcgttaagg gaggcaagcc cgacgtcgtc    1560
cagattgtcc gcaactacaa cgcctacctt cgggccagcg acgatctgcc taagatgttc    1620
atcgagtccg accctgggtt cttttccaac gctattgtcg agggagctaa gaagttccct    1680
aacaccgagt tcgtgaaggt gaagggcctc cacttcagcc aggaggacgc tccagatgaa    1740
atgggtaagt acatcaagag cttcgtggag cgcgtgctga agaacgagca ggaattcggc    1800
ggcggtggct cccatatgca atagcaatta ctcgaggaag acgccaaaaa cataaagaaa    1860
ggcccggcgc cattctatcc gctggaagat ggaaccgctg gagagcaact gcataaggct    1920
atgaagagat acgccctggt tcctggaaca attgcttta cagatgcaca tatcgaggtg    1980
gacatcactt acgctgagta cttcgaaatg tccgttcggt tggcagaagc tatgaaacga    2040
tatgggctga atacaaatca cagaatcgtc gtatgcagtg aaaactctct tcaattcttt    2100
atgccggtgt tgggcgcgtt atttatcgga gttgcagttg cgcccgcgaa cgacattat    2160 aatgaacgtg aattgctcaa cagtatgggc atttcgcagc ctaccgtggt gttcgtttcc    2220 aaaaagggg tgcaaaaaat tttgaacgtg caaaaaaagc tcccaatcat ccaaaaaatt    2280
attatcatgg attctaaaac ggattaccag ggatttcagt cgatgtacac gttcgtcaca    2340
tctcatctac ctcccggttt taatgaatac gattttgtgc cagagtcctt cgatagggac    2400 aagcaattg cactgatcat gaactcctct ggatctactg gtctgcctaa aggtgtcgct    2460
ctgcctcata gaactgcctg cgtgagattc tcgcatgcca gagatcctat ttttggcaat    2520
caaatcattc cggatactgc gattttaagt gttgttccat tccatcacgg ttttggaatg    2580
tttactacac tcggatattt gatatgtgga tttcgagtcg tcttaatgta tagatttgaa    2640
gaagagctgt ttctgaggag ccttcaggat tacaagattc aaagtgcgct gctggtgcca    2700
```

-continued

```
accctattct ccttcttcgc caaaagcact ctgattgaca aatacgattt atctaattta    2760
cacgaaattg cttctggtgg cgctcccctc tctaaggaag tcggggaagc ggttgccaag    2820
aggttccatc tgccaggtat caggcaagga tatgggctca ctgagactac atcagctatt    2880
ctgattacac ccgaggggga tgataaaccg ggcgcggtcg gtaaagttgt tccattttt    2940
gaagcgaagg ttgtggatct ggataccggg aaaacgctgg gcgttaatca agaggcgaa    3000
ctgtgtgtga gaggtcctat gattatgtcc ggttatgtaa acaatccgga agcgaccaac    3060
gccttgattg acaaggatgg atggctacat tctggagaca tagcttactg ggacgaagac    3120
gaacacttct tcatcgttga ccgcctgaag tctctgatta agtacaaagg ctatcaggtg    3180
gctcccgctg aattggaatc catcttgctc caacacccca acatcttcga cgcaggtgtc    3240
gcaggtcttc ccgacgatga cgccggtgaa cttcccgccg ccgttgttgt tttggagcac    3300
ggaaagacga tgacggaaaa agagatcgtg gattacgtcg ccagtcaagt aacaaccgcg    3360
aaaaagttgc gcggaggagt tgtgtttgtg gacgaagtac cgaaaggtct taccggaaaa    3420
ctcgacgcaa gaaaaatcag agagatcctc ataaaggcca agaagggcgg aaagatcgcc    3480
gtgtaagaat tctagagtcg gggcggccgg ccgcttcgag cagacatgat aagatacatt    3540
gatgagtttg gacaaaccac aactagaatg cagtgaaaaa aatgctttat ttgtgaaatt    3600
tgtgatgcta ttgctttatt tgtaaccatt ataagctgca ataaacaagt taacaacaac    3660
aattgcattc attttatgtt tcaggttcag ggggaggtgt gggaggtttt ttaaagcaag    3720
taaaacctct acaaatgtgg taaaatcgat aaggatccgt cgaccgatgc ccttgagagc    3780
cttcaaccca gtcagctcct tccggtgggc gcggggcatg actatcgtcg ccgcacttat    3840
gactgtcttc tttatcatgc aactcgtagg acaggtgccg gcagcgctct tccgcttcct    3900
cgctcactga ctcgctgcgc tcggtcgttc ggctgcggcg agcggtatca gctcactcaa    3960
aggcggtaat acggttatcc acagaatcag gggataacgc aggaaagaac atgtgagcaa    4020
aaggccagca aaaggccagg aaccgtaaaa aggccgcgtt gctggcgttt ttccataggc    4080
tccgcccccc tgacgagcat cacaaaaatc gacgctcaag tcagaggtgg cgaaacccga    4140
caggactata aagataccag gcgtttcccc ctggaagctc cctcgtgcgc tctcctgttc    4200
cgaccctgcc gcttaccgga tacctgtccg cctttctccc ttcgggaagc gtggcgcttt    4260
ctcatagctc acgctgtagg tatctcagtt cggtgtaggt cgttcgctcc aagctgggct    4320
gtgtgcacga accccccgtt cagcccgacc gctgcgcctt atccggtaac tatcgtcttg    4380
agtccaaccc ggtaagacac gacttatcgc cactggcagc agccactggt aacaggatta    4440
gcagagcgag gtatgtaggc ggtgctacag agttcttgaa gtggtggcct aactacggct    4500
acactagaag aacagtattt ggtatctgcg ctctgctgaa gccagttacc ttcggaaaaa    4560
gagttggtag ctcttgatcc ggcaaacaaa ccaccgctgg tagcggtggt ttttttgttt    4620
gcaagcagca gattacgcgc agaaaaaaag gatctcaaga agatcctttg atcttttcta    4680
cggggtctga cgctcagtgg aacgaaaact cacgttaagg gattttggtc atgagattat    4740
caaaaggat cttcacctag atccttttaa attaaaaatg aagttttaaa tcaatctaaa    4800
gtatatatga gtaaacttgg tctgacagcg gccgcaaatg ctaaaccact gcagtggtta    4860
ccagtgcttg atcagtgagg caccgatctc agcgatctgc ctatttcgtt cgtccatagt    4920
ggcctgactc cccgtcgtgt agatcactac gattcgtgag gcttaccat caggccccag    4980
cgcagcaatg atgccgcgag agccgcgttc accggccccc gatttgtcag caatgaacca    5040
gccagcaggg agggccgagc gaagaagtgg tcctgctact ttgtccgcct ccatccagtc    5100
```

-continued

| | |
|---|---:|
| tatgagctgc tgtcgtgatg ctagagtaag aagttcgcca gtgagtagtt tccgaagagt | 5160 |
| tgtggccatt gctactggca tcgtggtatc acgctcgtcg ttcggtatgg cttcgttcaa | 5220 |
| ctctggttcc cagcggtcaa gccgggtcac atgatcaccc atattatgaa gaaatgcagt | 5280 |
| cagctcctta gggcctccga tcgttgtcag aagtaagttg gccgcggtgt tgtcgctcat | 5340 |
| ggtaatggca gcactacaca attctcttac cgtcatgcca tccgtaagat gcttttccgt | 5400 |
| gaccggcgag tactcaacca agtcgttttg tgagtagtgt atacggcgac caagctgctc | 5460 |
| ttgcccggcg tctatacggg acaacaccgc gccacatagc agtactttga aagtgctcat | 5520 |
| catcgggaat cgttcttcgg ggcggaaaga ctcaaggatc ttgccgctat tgagatccag | 5580 |
| ttcgatatag cccactcttg cacccagttg atcttcagca tctttttactt tcaccagcgt | 5640 |
| ttcggggtgt gcaaaaacag gcaagcaaaa tgccgcaaag aagggaatga gtgcgacacg | 5700 |
| aaaatgttgg atgctcatac tcgtcctttt tcaatattat tgaagcattt atcagggtta | 5760 |
| ctagtacgtc tctcaaggat aagtaagtaa tattaaggta cgggaggtat tggacaggcc | 5820 |
| gcaataaaat atctttattt tcattacatc tgtgtgttgg ttttttgtgt gaatcgatag | 5880 |
| tactaacata cgctctccat caaaacaaaa cgaaacaaaa caaactagca aaataggctg | 5940 |
| tccccagtgc aagtgcaggt gccagaacat ttctct | 5976 |

<210> SEQ ID NO 23
<211> LENGTH: 2001
<212> TYPE: DNA
<213> ORGANISM: Homo sapiens

<400> SEQUENCE: 23

| | |
|---|---:|
| atgagggaac agctcaaagg ccacgagact caaacaactt gctgggacca tcccaaaatg | 60 |
| acagagctct accagtcttt agctgacctg aataatgtca gattctcagc ttataggact | 120 |
| gccatgaaac tccgaagact gcagaaggcc ctttgcttgg atctcttgag cctgtcagct | 180 |
| gcatgtgatg ccttggacca gcacaacctc aagcaaaatg accagcccat ggatatcctg | 240 |
| cagattatta attgtttgac cactatttat gaccgcctgg agcaagagca caacaatttg | 300 |
| gtcaacgtcc ctctctgcgt ggatatgtgt ctgaactggc tgctgaatgt ttatgatacg | 360 |
| ggacgaacag ggaggatccg tgtcctgtct tttaaaactg gcatcatttc cctgtgtaaa | 420 |
| gcacatttgg aagacaagta cagataccct ttcaagcaag tggcaagttc aacaggattt | 480 |
| tgtgaccagc gcaggctggg cctccttctg catgattcta tccaaattcc aagacagttg | 540 |
| ggtgaagttg catcctttgg gggcagtaac attgagccaa gtgtccggag ctgcttccaa | 600 |
| tttgctaata ataagccaga atcgaagcg ccctcttcc tagactggat gagactggaa | 660 |
| ccccagtcca tggtgtggct gcccgtcctg cacagagtgg ctgctgcaga aactgccaag | 720 |
| catcaggcca aatgtaacat ctgcaaagag tgtccaatca ttggattcag gtacaggagt | 780 |
| ctaaagcact taattatga catctgccaa agctgctttt tttctggtcg agttgcaaaa | 840 |
| ggccataaaa tgcactatcc catggtggaa tattgcactc cgactacatc aggagaagat | 900 |
| gttcgagact ttgccaaggt actaaaaaac aaatttcgaa ccaaaaggta ttttgcgaag | 960 |
| catccccgaa tgggctacct gccagtgcag actgtcttag aggggacaa catggaaact | 1020 |
| cccgttactc tgatcaactt ctggccagta gattctgcgc ctgcctcgtc ccctcagctt | 1080 |
| tcacacgatg atactcattc acgcattgaa cattatgcta gcaggctagc agaaatggaa | 1140 |
| aacagcaatg gatcttatct aaatgatagc atctctccta tgagagcat agatgatgaa | 1200 |
| catttgttaa tccagcatta ctgccaaagt ttgaaccagg actccccccct gagccagcct | 1260 |

```
cgtagtcctg cccagatctt gatttcctta gagagtgagg aaagagggga gctagagaga    1320
atcctagcag atcttgagga agaaaacagg aatctgcaag cagaatatga ccgtctaaag    1380
cagcagcacg aacataaagg cctgtcccca ctgccgtccc ctcctgaaat gatgcccacc    1440
tctccccaga gtccccggga tgctgagctc attgctgagg ccaagctact gcgtcaacac    1500
aaaggccgcc tggaagccag gatgcaaatc ctggaagacc acaataaaca gctggagtca    1560
cagttacaca ggctaaggca gctgctggag caacccagg cagaggccaa agtgaatggc    1620
acaacggtgt cctctccttc tacctctcta cagaggtccg acagcagtca gcctatgctg    1680
ctccgagtgg ttggcagtca aacttcggac tccatgggtg aggaagatct tctcagtcct    1740
ccccaggaca caagcacagg gttagaggag gtgatggagc aactcaacaa ctccttccct    1800
agttcaagag gacacaatgt aggaagtctt ttccacatgg cagatgattt gggcagagcg    1860
atggagtcct tagtatcagt catgacagat gaagaaggag cagaaacgcg tacgcggccg    1920
ctcgagcaga aactcatctc agaagaggat ctggcagcaa atgatatcct ggattacaag    1980
gatgacgacg ataaggttta a                                              2001

<210> SEQ ID NO 24
<211> LENGTH: 243
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk

<400> SEQUENCE: 24
ctgcagtatt tagcatgccc cacccatctg caaggcattc tggatagtgt caaaacagcc      60
ggaaatcaag tccgtttatc tcaaacttta gcattttggg aataaatgat atttgctatg    120
ctggttaaat tagattttag ttaaatttcc tgctgaagct ctagtacgat aagtaacttg    180
acctaagtgt aaagttgaga tttccttcag gtttatatag cttgtgcgcc gcctgggtac    240
ctc                                                                   243

<210> SEQ ID NO 25
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-for

<400> SEQUENCE: 25
cgggatccct gcagtattta gcatg                                            25

<210> SEQ ID NO 26
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Arg-UGA-rev

<400> SEQUENCE: 26
atccattagg ccacgtggtc cgaggtaccc aggcggcg                              38
```

<210> SEQ ID NO 27
<211> LENGTH: 61
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Arg-for

<400> SEQUENCE: 27
cgccgcctgg gtacctcgga ccacgtggcc taatggataa ggcgtctgac ttcagatcag    60
a    61

<210> SEQ ID NO 28
<211> LENGTH: 62
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Arg-rev

<400> SEQUENCE: 28
gaagatctaa aaaaccacg aagggattcg aaccctcaat cttctgatct gaagtcagac    60
gc    62

<210> SEQ ID NO 29
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Arg(UGA)-rev

<400> SEQUENCE: 29
gaagatctaa aaaaccacg aaggg    25

<210> SEQ ID NO 30
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Trp-UGA-rev

<400> SEQUENCE: 30
ttgcgccacg aggtcgaggt acccaggcg    29

<210> SEQ ID NO 31
<211> LENGTH: 61
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Trp-for

<400> SEQUENCE: 31
cgccgcctgg gtacctcgac ctcgtggcgc aacggcagcg cgtctgactt cagatcagaa    60
g    61

<210> SEQ ID NO 32
<211> LENGTH: 62
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Trp-rev

<400> SEQUENCE: 32
gaagatctaa aaagaccccg acgtgatttg aacacgcaac cttctgatct gaagtcagac    60
gc    62

<210> SEQ ID NO 33
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Trp(UGA)-rev

<400> SEQUENCE: 33
gaagatctaa aaagaccccg acgtg    25

<210> SEQ ID NO 34
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Gly-UGA-rev

<400> SEQUENCE: 34
taaccactat accaccaacg cgaggtaccc aggcggcg    38

<210> SEQ ID NO 35
<211> LENGTH: 60
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Gly-for

<400> SEQUENCE: 35
cgccgcctgg gtacctcgcg ttggtggtat agtggttagc atagctgcct tcaaagcagt    60

<210> SEQ ID NO 36
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Gly-rev

<400> SEQUENCE: 36
gaagatctaa aaatgcgttg gccgggaatc gaacccgggt caactgcttt gaaggcagc    59

-continued

```
<210> SEQ ID NO 37
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Gly(UGA)-rev

<400> SEQUENCE: 37
gaagatctaa aaatgcgttg gccg                                         24

<210> SEQ ID NO 38
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Cys-UGA-rev

<400> SEQUENCE: 38
tgagccctac ccccgaggta cccaggcgg                                    29

<210> SEQ ID NO 39
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Cys-for

<400> SEQUENCE: 39
cgccgcctgg gtacctcggg ggtagggctc aggatagag catttgactt cagatcaag    59

<210> SEQ ID NO 40
<211> LENGTH: 60
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Cys-rev

<400> SEQUENCE: 40
gaagatctaa aaggggca cctagattcg aaccggggac ctcttgatct gaagtcaaat    60

<210> SEQ ID NO 41
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Cys(UGA)-rev

<400> SEQUENCE: 41
gaagatctaa aaggggggca cc                                           22

<210> SEQ ID NO 42
<211> LENGTH: 32
<212> TYPE: DNA
<213> ORGANISM: Artificial Sequence
```

```
<220> FEATURE:
<223> OTHER INFORMATION: Synthetic Polynucleotide
<220> FEATURE:
<221> NAME/KEY: misc_feature
<223> OTHER INFORMATION: 7sk-UGA-Leu-rev

<400> SEQUENCE: 42
gctctgccat cttaacgagg tacccaggcg gc                                32

<210> SEQ ID NO 43
<211> LENGTH: 62
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Leu-for

<400> SEQUENCE: 43
gccgcctggg tacctcgtta agatggcaga gcccggcaat tgcataagac ttcaaacttt    60
at                                                                  62

<210> SEQ ID NO 44
<211> LENGTH: 62
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Leu-rev

<400> SEQUENCE: 44
gaagatctaa aaagttaatg agaggagttg aacctctgat tataaagttt gaagtcttat    60
gc                                                                  62

<210> SEQ ID NO 45
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Leu-rev(2)

<400> SEQUENCE: 45
gaagatctaa aaagttaatg agagg                                         25

<210> SEQ ID NO 46
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-UGA-Ser-rev

<400> SEQUENCE: 46
ttaaccactc ggccacgact acgaggtacc caggcggc                           38

<210> SEQ ID NO 47
<211> LENGTH: 68
<212> TYPE: DNA
<213> ORGANISM: Artificial Sequence
```

<220> FEATURE:
<223> OTHER INFORMATION: Synthetic Polynucleotide
<220> FEATURE:
<221> NAME/KEY: misc_feature
<223> OTHER INFORMATION: UGA-Ser-for

<400> SEQUENCE: 47
gcgccgcctg ggtacctcgt agtcgtggcc gagtggttaa ggcgatggac ttcaaatcca    60
ttggggtt                                                              68

<210> SEQ ID NO 48
<211> LENGTH: 67
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Ser-rev

<400> SEQUENCE: 48
gaagatctaa aaacgtagtc ggcaggattc gaacctgcgc ggggaaaccc caatggattt    60
gaagtcc                                                               67

<210> SEQ ID NO 49
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UGA-Ser-rev(2)

<400> SEQUENCE: 49
gaagatctaa aaacgtagtc ggcagg                                          26

<210> SEQ ID NO 50
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Glu-UAA-rev

<400> SEQUENCE: 50
actagaccac cagggagagg tacccaggcg                                      30

<210> SEQ ID NO 51
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Glu-for

<400> SEQUENCE: 51
cgccgcctgg gtacctctcc ctggtggtct agtggctagg attcggcgct ttaaccgcc     59

<210> SEQ ID NO 52
<211> LENGTH: 59
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<223> OTHER INFORMATION: UAA-Glu-rev

<400> SEQUENCE: 52
gaagatctaa aaaattcctg gccgggaatc gaacccgggg cgcggcggtt aaagcgccg      59

<210> SEQ ID NO 53
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Glu-UAA-rev

<400> SEQUENCE: 53
gaagatctaa aaaattcctg gccgg                                           25

<210> SEQ ID NO 54
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Gln-UAA-rev

<400> SEQUENCE: 54
attacaccat gggaccgagg tacccaggcg                                      30

<210> SEQ ID NO 55
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Gln-for

<400> SEQUENCE: 55
cgccgcctgg gtacctcggt cccatggtgt aatggttagc actctggact ttaaatcca     59

<210> SEQ ID NO 56
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Gln-rev

<400> SEQUENCE: 56
gaagatctaa aaaaggtccc accgagattt gaactcggat cgctggattt aaagtccag     59

<210> SEQ ID NO 57
<211> LENGTH: 24
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<223> OTHER INFORMATION: Gln-UAA-rev

<400> SEQUENCE: 57
gaagatctaa aaaaggtccc accg                                              24

<210> SEQ ID NO 58
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Lys-UAA-rev

<400> SEQUENCE: 58
actgagctat ccgggcgagg tacccaggcg                                        30

<210> SEQ ID NO 59
<211> LENGTH: 60
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Lys-for

<400> SEQUENCE: 59
cgccgcctgg gtacctcgcc cggatagctc agtcggtaga gcatcagact ttaaatctga      60

<210> SEQ ID NO 60
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Lys-rev

<400> SEQUENCE: 60
gaagatctaa aaacgcccga acagggactt gaaccctgga ccctcagatt taaagtctg      59

<210> SEQ ID NO 61
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Lys-UAA-rev

<400> SEQUENCE: 61
gaagatctaa aaacgcccga acagg                                             25

<210> SEQ ID NO 62
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-UAA-Leu-rev
```

<400> SEQUENCE: 62
gctctgccat cttaacgagg tacccaggcg gc                                32

<210> SEQ ID NO 63
<211> LENGTH: 63
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Leu-for

<400> SEQUENCE: 63
gcgccgcctg ggtacctcgt taagatggca gagcccggca attgcataag actttaaact    60
tta                                                                 63

<210> SEQ ID NO 64
<211> LENGTH: 62
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Leu-rev

<400> SEQUENCE: 64
gaagatctaa aaagttaatg agaggagttg aacctctgat tataaagttt aaagtcttat    60
gc                                                                  62

<210> SEQ ID NO 65
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Leu-rev(2)

<400> SEQUENCE: 65
gaagatctaa aaagttaatg agaggag                                       27

<210> SEQ ID NO 66
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-UAA-Ser-rev

<400> SEQUENCE: 66
tcggccacga ctacgaggta cccaggcggc                                    30

<210> SEQ ID NO 67
<211> LENGTH: 68
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Ser-for

<400> SEQUENCE: 67
gcgccgcctg ggtacctcgt agtcgtggcc gagtggttaa ggcgatggac tttaaatcca        60
ttgggggtt                                                                68

<210> SEQ ID NO 68
<211> LENGTH: 67
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Ser-rev

<400> SEQUENCE: 68
gaagatctaa aaacgtagtc ggcaggattc gaacctgcgc ggggaaaccc caatggattt        60
aaagtcc                                                                  67

<210> SEQ ID NO 69
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAA-Ser-rev(2)

<400> SEQUENCE: 69
gaagatctaa aaacgtagtc ggcagg                                             26

<210> SEQ ID NO 70
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-UAG-Leu-rev

<400> SEQUENCE: 70
actcggccat cctgacgagg tacccaggcg gc                                      32

<210> SEQ ID NO 71
<211> LENGTH: 66
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAG-Leu-for

<400> SEQUENCE: 71
gccgcctggg tacctcgtca ggatggccga gtggtctaag gcgccagact ctagttctgg        60
tctcca                                                                   66

<210> SEQ ID NO 72
<211> LENGTH: 63
<212> TYPE: DNA
<213> ORGANISM: Artificial Sequence
<220> FEATURE:
<223> OTHER INFORMATION: Synthetic Polynucleotide

```
<220> FEATURE:
<221> NAME/KEY: misc_feature
<223> OTHER INFORMATION: UAG-Leu-rev

<400> SEQUENCE: 72
gaagatctaa aaagtcagaa gtgggattcg aacccacgcc tccattggag accagaacta      60
gag                                                                   63

<210> SEQ ID NO 73
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAG-Leu-rev(2)

<400> SEQUENCE: 73
gaagatctaa aaagtcagaa gtggg                                           25

<210> SEQ ID NO 74
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-UAG-Glu-rev

<400> SEQUENCE: 74
actagaccac cagggagagg tacccaggc                                       29

<210> SEQ ID NO 75
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAG-Glu-for

<400> SEQUENCE: 75
ccgcctgggt acctctccct ggtggtctag tggttaggat tcggcgctct aaccgccgc      59

<210> SEQ ID NO 76
<211> LENGTH: 62
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAG-Glu-rev

<400> SEQUENCE: 76
gaagatctaa aaattccctg accgggaatc gaacccgggc cgcggcggtt agagcgccga      60
at                                                                   62

<210> SEQ ID NO 77
<211> LENGTH: 26
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<223> OTHER INFORMATION: UAG-Glu-rev(2)

<400> SEQUENCE: 77
gaagatctaa aaattccctg accggg                                          26

<210> SEQ ID NO 78
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Gln-UGA for

<400> SEQUENCE: 78
ctcggatcgc tggatttgaa gtccagagtg ctaac                                35

<210> SEQ ID NO 79
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Gln-UGA rev

<400> SEQUENCE: 79
gttagcactc tggacttcaa atccagcgat ccgag                                35

<210> SEQ ID NO 80
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Tyr-UAA for

<400> SEQUENCE: 80
gcgacctaag gatctaaagt cctccgctct acc                                  33

<210> SEQ ID NO 81
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Tyr-UAA rev

<400> SEQUENCE: 81
ggtagagcgg aggactttag atccttaggt cgc                                  33

<210> SEQ ID NO 82
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 7sk-Trp-UAG-for
```

```
<400> SEQUENCE: 82
gcaacggcag cgcgtctgac tctagatcag aaggt                    35

<210> SEQ ID NO 83
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: UAG-Trp-rev

<400> SEQUENCE: 83
accttctgat ctagagtcag acgcgctgcc gttgc                    35

<210> SEQ ID NO 84
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAG-for

<400> SEQUENCE: 84
ggcgagggcg atgccaccta gggcaagctg accctgaagt tc            42

<210> SEQ ID NO 85
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAG-for

<400> SEQUENCE: 85
gaacttcagg gtcagcttgc cctaggtggc atcgccctcg cc            42

<210> SEQ ID NO 86
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAA-for

<400> SEQUENCE: 86
ggcgagggcg atgccaccta aggcaagctg accctgaagt tc            42

<210> SEQ ID NO 87
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAA-for

<400> SEQUENCE: 87
gaacttcagg gtcagcttgc cttaggtggc atcgccctcg cc            42
```

```
<210> SEQ ID NO 88
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAG-for

<400> SEQUENCE: 88
ggcgagggcg atgccacctg aggcaagctg accctgaagt tc          42

<210> SEQ ID NO 89
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAG-for

<400> SEQUENCE: 89
gaacttcagg gtcagcttgc ctcaggtggc atcgccctcg cc          42
```